(12) United States Patent
Kelley et al.

(10) Patent No.: US 11,351,130 B2
(45) Date of Patent: Jun. 7, 2022

(54) PREVENTION AND REVERSAL OF INFLAMMATION INDUCED DNA DAMAGE

(71) Applicant: Indiana University Research and Technology Corporation, Indianapolis, IN (US)

(72) Inventors: Mark R. Kelley, Zionsville, IN (US); Jill Fehrenbacher, Indianapolis, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 0 days.

(21) Appl. No.: 16/850,436

(22) Filed: Apr. 16, 2020

(65) Prior Publication Data

US 2020/0253904 A1 Aug. 13, 2020

Related U.S. Application Data

(63) Continuation of application No. 16/092,816, filed as application No. PCT/US2018/027786 on Apr. 16, 2018, now abandoned.

(60) Provisional application No. 62/486,033, filed on Apr. 17, 2017.

(51) Int. Cl.
| | |
|---|---|
| *A61K 31/192* | (2006.01) |
| *A61K 45/06* | (2006.01) |
| *A61K 31/165* | (2006.01) |
| *A61K 31/201* | (2006.01) |
| *A61K 31/555* | (2006.01) |
| *A61K 31/282* | (2006.01) |
| *A61K 33/243* | (2019.01) |
| *A61P 25/02* | (2006.01) |
| *A61N 5/00* | (2006.01) |

(52) U.S. Cl.
CPC .......... *A61K 31/192* (2013.01); *A61K 31/165* (2013.01); *A61K 31/201* (2013.01); *A61K 31/555* (2013.01); *A61K 33/243* (2019.01); *A61K 45/06* (2013.01); *A61N 5/00* (2013.01); *A61P 25/02* (2018.01); *A61K 31/282* (2013.01)

(58) Field of Classification Search
CPC .. A61K 31/165; A61K 31/122; A61K 31/201; A61K 31/555; A61K 31/192; A61K 31/282; A61K 33/24; A61K 33/243; A61K 45/06; A61P 25/02; A61N 5/00
See application file for complete search history.

(56) References Cited

U.S. PATENT DOCUMENTS

| | | |
|---|---|---|
| 2003/0203960 A1 | 10/2003 | Hausheer |
| 2003/0229004 A1 | 12/2003 | Zarling et al. |
| 2011/0311452 A1 | 12/2011 | Ferrari et al. |
| 2014/0128398 A1 | 5/2014 | Kelley et al. |

FOREIGN PATENT DOCUMENTS

| | | | | |
|---|---|---|---|---|
| EP | 0801949 A1 | * | 10/1997 | ............. A61K 31/19 |
| EP | 0813866 A2 | | 12/1997 | |
| WO | 2009042542 A1 | | 4/2009 | |
| WO | 2012073041 A2 | | 6/2012 | |
| WO | 2012148889 A1 | | 11/2012 | |
| WO | WO-2012162589 A1 | * | 11/2012 | ............. A61P 11/00 |
| WO | 2018161741 A1 | | 9/2018 | |

OTHER PUBLICATIONS

Fishel et. al., Mol. Aspects Med., publ. 2007, Elsevier, vol. 28, pp. 375-395 (Year: 2007).*
Neumann et al., Inflammatory pain hypersensitivity mediated by phenotypic switch in myelinated primary sensory neurons. Nature, 1996, vol. 384, pp. 360-364.
Pastukh et al., An oxidative DNA "damage" and repair mechanism localized in the VEGF promoter is important for hypoxia-induced VEGF mRNA expression. Am J Physiol Lung Cell Mol Physiol., 2015, vol. 309, pp. L1367-L1375.
Poltorak et al., Defective LPS signaling in C3H/HeJ and C57BL/10ScCr mice: mutations in Tlr4 gene. Science, 1998, vol. 282, pp. 2085-2088.
Qin et al., CCL2 and CXCL1 trigger calcitonin gene-related peptide release by exciting primary nociceptive neurons. Journal of neuroscience research, 2005, vol. 82, pp. 51-62.
Remans et al., Intracellular free radical production in synovial T lymphocytes from patients with rheumatoid arthritis. Arthritis and rheumatism, 2005, vol. 52, pp. 2003-2009.
Richardson et al., Cellular mechanisms of neurogenic inflammation. J Pharmacol Exp Ther., 2002, vol. 302, pp. 839-845.
Rogakou et al., DNA double-stranded breaks induce histone H2AX phosphorylation on serine 139. J Biol Chem., 1998, vol. 273, pp. 5858-5868.
Rollins et al., Chemokines. Blood, 1997, vol. 90, pp. 909-928.
Ziel et al., Ref-1/Ape is critical for formation of the hypoxia-inducible transcriptional complex on the hypoxic response element of the rat pulmonary artery endothelial cell VEGF gene. Faseb J., 2004, vol. 18, pp. 986-988.
Safieh-Garabedian et al., Contribution of interleukin-1 beta to the inflammation-induced increase in nerve growth factor levels and inflammatory hyperalgesia. Br J Pharmacol., 1995, vol. 115, pp. 1265-1275.

(Continued)

*Primary Examiner* — Sarah Pihonak
(74) *Attorney, Agent, or Firm* — Stinson LLP

(57) ABSTRACT

Methods of reducing neuronal sensitivity, thereby reducing inflammation and chronic pain, in subjects having diabetes are disclosed herein. Particularly disclosed are methods of administrating the apurinic/apyrimidinic endonuclease 1 redox factor 1 (APE 1/Ref-1) inhibitor, APX3330, to enhance the DNA base excision repair (BER) pathway, thereby reducing neuronal sensitivity to inflammatory mediators and alleviating inflammatory or chronic pain.

14 Claims, 25 Drawing Sheets

Specification includes a Sequence Listing.

(56) References Cited

OTHER PUBLICATIONS

Salvemini et al., Roles of reactive oxygen and nitrogen species in pain. Free radical biology & medicine, 2011, vol. 51, pp. 951-966.
Sauer et al., Reactive oxygen species as intracellular messengers during cell growth and differentiation. Cell Physiol Biochem., 2001, vol. 11, pp. 173-186.
Sawada et al., Activation of transient receptor potential ankyrin 1 by hydrogen peroxide. Eur J Neurosci. 2008, vol. 27, pp. 1131-1142.
Shigenaga et al., Oxidative damage and mitochondrial decay in aging. Proc Natl Acad Sci U S A, 1994, vol. 91, pp. 10771-10778.
Stein et al., Unilateral inflammation of the hindpaw in rats as a model of prolonged noxious stimulation: alterations in behavior and nociceptive thresholds. Pharmacol Biochem Behav., 1988, vol. 31, pp. 445-451.
Tanaka et al., Monocyte chemoattractant protein-1/CC chemokine ligand 2 enhances apoptotic cell removal by macrophages through Rac1 activation. Biochem Biophys Res Commun., 2010, vol. 399, pp. 677-682.
Tse et al., Lipopolysaccharide differentially modulates expression of cytokines and cyclooxygenases in dorsal root ganglion cells via Toll-like receptor-4 dependent pathways. Neuroscience, 2014, vol. 267, pp. 241-251.
Vasko et al., The multifunctional DNA repair/redox enzyme Ape1/Ref-1 promotes survival of neurons after oxidative stress. DNA repair, 2005, vol. 4, pp. 367-379.
Vasko et al., The repair function of the multifunctional DNA repair/redox protein APE1 is neuroprotective after ionizing radiation. DNA repair, 2011, vol. 10, pp. 942-952.
White et al., Excitatory monocyte chemoattractant protein-1 signaling is up-regulated in sensory neurons after chronic compression of the dorsal root ganglion. Proc Natl Acad Sci U S A, 2005, vol. 102, pp. 14092-14097.
Williams et al., Eicosanoids and inflammation. J Pathol., 1088, vol. 156, pp. 101-110.
Woolf et al., Eicosanoids and inflammation. J Pathol., 1988, vol. 156, pp. 101-110.
Yamasaki et al., Role of CCR2 in immunobiology and neurobiology. Clinical and Experimental Neuroimmunology, 2012, vol. 3, pp. 16-29.
Zhang et al., Induction of monocyte chemoattractant protein-1 (MCP-1) and its receptor CCR2 in primary sensory neurons contributes to paclitaxel-induced peripheral neuropathy. J Pain, 2013, vol. 14, pp. 1031-1044.
Zhang et al., Toll-like receptor 4 signaling: A common pathway for interactions between prooxidants and extracellular disulfide high mobility group box 1 (HMGB1) protein-coupled activation. Biochemical pharmacology, 2015, vol. 98, pp. 132-143.
Zhao et al., PKC-NF-kappaB are involved in CCL2-induced Nav1.8 expression and channel function in dorsal root ganglion neurons 2014, Biosci Rep 34.
Kelley et al., Identification and Characterization of New Chemical Entities Targeting Apurinic/Apyrimidinic Endonuclease 1 for the Prevention for Chemotherapy-induced Peripheral Neuropathy; The Journal of Pharmacology and Experimental Therapeutics; 10-pages.
Manabe, Ichiro; Chronic Inflammatioon Links Cardiovascular, Metabolic and Renal Diseases; Circulation Journal; 2011, vol. 75, pp. 2739-2748.
Lipnik-Stangelj, Metoda; Mediators of Inflammation as Targets for Chronic Pain Treatment; Hindawi Publishing Corporation, Mediators of Inflammation; vol. 2013, Article ID 783235, 3-pages.
Krein et al., The Effect of Chronic Pain on Diabetes Patients' Self-Managment; Epidemiology/Health Services/Psychosocial Research; 6-pages.
Aguilera-Aguirre et al., Innate inflammation induced by the 8-oxoguanine DNA glycosylase-1-KRAS-NF-kappaB pathway. J Immunol; 2014, vol. 193, pp. 4643-4653.
Ahles et al., Candidate mechanisms for chemotherapy-induced cognitive changes. Nature reviews Cancer; 2007, vol. 7, pp. 192-201.

Andersson et al., Transient Receptor Potential A1 is a Sensory Receptor for Multiple Products of Oxidative Stress; Cellular/Molecular, The Journal of Neuroscience, 2008, vol. 28, No. 10, pp. 2485-2494.
Babior B.M., Phagocytes and oxidative stress. The American journal of medicine; 2000, vol. 109, pp. 33-44.
Barzilai et al., The role of the DNA damage response in neuronal development, organization and maintenance. DNA Repair; (Amst), vol. 7, pp. 1010-1027.
Bauerova et al., Role of reactive oxygen and nitrogen species in etiopathogenesis of rheumatoid arthritis. General physiology and biophysics, 1999, vol. 18, pp. 15-20.
Brooks P.J., DNA repair in neural cells: basic science and clinical implications. Mutat Res., 2002, vol. 509, pp. 93-108.
Calil et al., Lipopolysaccharide induces inflammatory hyperalgesia triggering a TLR4/MyD88-dependent cytokine cascade in the mice paw; PLoS One, 2014, vol. 9, pp. e90013.
Charo et al., Molecular cloning and functional expression of two monocyte chemoattractant protein 1 receptors reveals alternative splicing of the carboxyl-terminal tails. Proc Natl Acad Sci U S A; 2014, vol. 91, pp. 2752-2756.
Cunha et al., The pivotal role of tumour necrosis factor alpha in the development of inflammatory hyperalgesia. Br J Pharmacol; 1992, vol. 107, pp. 660-664.
Capuano et al., Proinflammatory-activated trigeminal satellite cells promote neuronal sensitization: relevance for migraine pathology; 2009, Molecular Pain, vol. 5, 13 pages.
David et al., Base-excision repair of oxidative DNA damage. Nature, 2007, vol. 447, pp. 941-950.
Ding et al., Advanced oxidation protein products sensitized the transient receptor potential vanilloid 1 via NADPH oxidase 1 and 4 to cause mechanical hyperalgesia. Redox Biol., 2016, vol. 10, pp. 1-11.
Diogenes et al., LPS sensitizes TRPV1 via activation of TLR4 in trigeminal sensory neurons. Journal of dental research, 2011, vol. 90, pp. 759-764.
Duggett et al., Oxidative stress in the development, maintenance and resolution of paclitaxel-induced painful neuropathy. Neuroscience, 2016, vol. 333, pp. 13-26.
Ferreira et al., Interieukin-1 beta as a potent hyperalgesic agent antagonized by a tripeptide analogue. Nature, 1988, vol. 334, pp. 698-700.
Ferreira et al., Bradykinin initiates cytokine-mediated inflammatory hyperalgesia. British journal of pharmacology; 1993, vol. 110, pp. 1227-1231.
Fidanboylu et al., Global inhibition of reactive oxygen species (ROS) inhibits paclitaxel-induced painful peripheral neuropathy. PLoS One; 2011, vol. 6, pp. e25212.
Fishel et al., Manipulation of base excision repair to sensitize ovarian cancer cells to alkylating agent temozolomide. Clin Cancer Res; 2007a, vol. 13, pp. 260-267.
Fishel et al., DNA repair in neurons: so if they don't divide what's to repair? Mutat Res., 2007b, vol. 614, pp. 24-36.
Fortini et al., Mechanisms of dealing with DNA damage in terminally differentiated cells. Mutat Res., 2007, vol. 685, pp. 38-44.
Gillespie et al., Oxidative DNA modifications in hypoxic signaling. Ann N Y Acad Sci., 2009, vol. 1177, pp. 140-150.
Hetman et al., Neurotoxic mechanisms of DNA damage: focus on transcriptional inhibition. J Neurochem., 2010, vol. 114, pp. 1537-1549.
Holmstrom et al., Cellular mechanisms and physiological consequences of redox-dependent signalling. Nat Rev Mol Cell Biol., 2014, vol. 15, pp. 411-421.
Hou et al., PKC and PKA, but not PKG mediate LPS-induced CGRP release and [Ca(2+)](i) elevation in DRG neurons of neonatal rats. Journal of neuroscience research, 2001, vol. 66, pp. 592-600.
Abbadie et al., Chemokines and Pain Mechanisms, Brain Res Rev., 2009, vol. 60, No. 1, pp. 125-134.
Al-Mehdi et al., Perinuclear Mitochondrial Clustering Creates and Oxidant-Rich Nuclear Domain Requireed for Hypoxia-Incuced Transcription; Sci Signal, vol. 5, 20 pages.

(56) References Cited

OTHER PUBLICATIONS

Izumi et al., Effects of backbone contacts 3' to the abasic site on the cleavage and the product binding by human apurinic/apyrimidinic endonuclease (APE1). Biochemistry, 2004, vol. 43, pp. 684-689.
Jedinak et al., Apurinic/Apyrimidinic endonuclease 1 regulates inflammatory response in macrophages. Anticancer Res., 2011, vol. 31, pp. 379-385.
Jeon et al., Monocyte chemoattractant protein-1 immunoreactivity in sensory ganglia and hindpaw after adjuvant injection. Neuroreport, 2008, vol. 19, pp. 183-186.
Jiang et al., Role of APE1 in differentiated neuroblastoma SH-SY5Y cells in response to oxidative stress: use of APE1 small molecule inhibitors to delineate APE1 functions. DNA repair, 2009, vol. 8, pp. 1273-1282.
Jiang et al., Implications of apurinic/apyrimidinic endonuclease in reactive oxygen signaling response after cisplatin treatment of dorsal root ganglion neurons. Cancer Research, 2008a, vol. 68, pp. 6425-6434.
Neurotoxicity Detoxification I Brain & BodyWorks in Jupiter, FL; May 31, 2018; 3-pages.
Kao et al., CC chemokine ligand 2 upregulates the current density and expression of TRPV1 channels and Nav1.8 sodium channels in dorsal root ganglion neurons. J Neuroinflammation, 2012, vol. 9, pp. 189.
Keeble et al., Hydrogen peroxide is a novel mediator of inflammatory hyperalgesia, acting via transient receptor potential vanilloid 1-dependent and independent mechanisms. Pain, 2009, vol. 141, pp. 135-142.
Kelley et al., Role of the DNA base excision repair protein, APE1 in cisplatin, oxaliplatin, or carboplatin induced sensory neuropathy. PLoS One, 2014, vol. 9, pp. e106485.
Kelley et al., Challenges and opportunities identifying therapeutic targets fro chemotherapy-induces peripheral neuropathy resulting from oxidative DNA damage; Neural Regen Res., 2017, vol. 12, No. 1, pp. 72-74.

Miller et al., Damage-associated molecular patterns generated in osteoarthritis directly excite murine nociceptive neurons through Toll-like receptor 4. Arthritis Rheumatol. 2015, vol. 67, pp. 2933-2943.
Kim et al., Reactive oxygen species (ROS) play an important role in a rat model of neuropathic pain. Pain, 2004, vol. 111, pp. 116-124.
Kisby et al., Damage and repair of nerve cell DNA in toxic stress. Drug metabolism reviews, 1999, vol. 31, pp. 589-618.
Kruman et al., DNA damage response and neuroprotection. Frontiers in bioscience : a journal and virtual library, 2008, vol. 13, pp. 2504-2515.
Li et al., The Cancer Chemotherapeutic Paclitaxel Increases Human and Rodent Sensory Neuron Responses to TRPV1 by Activation of TLR4. J Neurosci., 2015, vol. 35, pp. 13487-13500.
Li et al., Toll-like receptor 4 signaling contributes to Paclitaxel-induced peripheral neuropathy. J Pain, 2014, vol. 15, pp. 712-725.
Lin et al., H2O2 generated by NADPH oxidase 4 contributes to transient receptor potential vanilloid 1 channel-mediated mechanosensation in the rat kidney. Am J Physiol Renal Physiol. 2015, vol. 309, pp. F369-F376.
Luo et al., Role of the multifunctional DNA repair and redox signaling protein Ape1/Ref-1 in cancer and endothelial cells: small-molecule inhibition of the redox function of Ape1. Antioxidants & redox signaling, 2008, vol. 10, pp. 1853-1867.
Martin et al., Reactive oxygen species as double-edged swords in cellular processes: low-dose cell signaling versus high-dose toxicity. Hum Exp Toxicol., 2002, vol. 21, pp. 71-75.
McMurray et al., To die or not to die: DNA repair in neurons. Mutat Res., 2005, vol. 577, pp. 260-274.
Meseguer et al., TRPA1 channels mediate acute neurogenic inflammation and pain produced by bacterial endotoxins. Nat Commun., 2004, vol. 5, pp. 3125.
Miller et al., CCR2 chemokine receptor signaling mediates pain in experimental osteoarthritis; PNAS, 2012, 6-pages.
Masakazu et al., Reactive Oxygen Species Derived from NOX1/NADPH Oxidase Enhance Inflammatory Pain; The Journal of Neuroscience, 2008, vol. 28, No. 38, pp. 9486-9494.

\* cited by examiner

| | Reporter Transactivation Assay IC50 μM | Tumor Cell Killing IC50 μM | Increase in APE1 DNA repair activity[6] | $t_{1/2}$ hrs[4] | P450 Metabolism $t_{1/2}$ min[5] |
|---|---|---|---|---|---|
| E3330 | 45[1] | 26[1] | 25 - 50 μM[1] | 3.6 | 20 |
| APX2007 | 7 | 3.6 - 6.2[2] | ND | 2.9 | |
| APX2009 | 7 | 3 - 6[2]<br>2.5 - 5.0[3] | 0.125 μM | 25.8 | 173 |
| APX2032 | 7 | 4 - 25[2] | ND | 2.8 | |
| | | | | | |
| APX2009 increase in activity vs. E3330 (fold) | 6.4 | 4.3 - 8.7 | 200 | 7.2 | 8.7 |

FIG. 10

Avg IC50 Values for IMR32 Cells
p53wt, MYCN amplified

| Compound | IC50 (µM) | SEM |
|---|---|---|
| E3330 | 25.14 | 1.38 |
| APX2007 | 3.58 | 1.38 |
| APX2009 | 3.00 | 0.41 |
| APX2032 | 2.47 | 0.27 |

FIG. 11A

Avg IC50 Values for SK-N-SH Cells
p53wt, MYCN non-amplified

| Compound | IC50 (µM) | SEM |
|---|---|---|
| E3330 | 27.30 | 0.97 |
| APX2007 | 6.23 | 1.1 |
| APX2009 | 5.96 | 0.57 |
| APX2032 | 4.37 | 0.22 |

FIG. 11B

PREVENTION AND REVERSAL OF INFLAMMATION INDUCED DNA DAMAGE

CROSS-REFERENCE OT RELATED APPLICATIONS

This application is a continuation application based on U.S. patent application Ser. No. 16/092,816, filed Oct. 11, 2018, which is a U.S. National Phase Application of PCT/US2018/27786, filed Apr. 16, 2018, which claims priority to U.S. Provisional Patent Application No. 62/486,033, filed on Apr. 17 2017, which are hereby incorporated by reference in their entireties.

STATEMENT OF GOVERNMENT SUPPORT

This invention was made with government support under NS091667 awarded by the National Institutes of Health (NIH). The government has certain rights in the invention.

INCORPORATION OF SEQUENCE LISTING

A computer readable form of the Sequence Listing containing the file named "IURTC_2017-116-08_ST25.txt", which is 1,160 bytes in size (as measured in MICROSOFT WINDOWS® EXPLORER), is provided herein and is herein incorporated by reference. This Sequence Listing consists of SEQ ID NOs: 1-4.

BACKGROUND OF THE DISCLOSURE

The present disclosure relates generally to methods of reducing neuronal sensitivity, thereby reducing inflammation and chronic pain. Particularly, it has been found herein that by enhancing the DNA base excision repair (BER) pathway, through the administration of APX3330, neuronal sensitivity to inflammatory mediators is reduced, thereby alleviating inflammatory or chronic pain.

Inflammatory mediators, released from damaged tissue and immune cells during damage, can have acute and chronic effects on the sensitivity of primary sensory neurons. Prostaglandins, bradykinin, histamine, serotonin, tryptases, cytokines, and ATP can alter the sensitivity of sensory neurons to various stimuli via posttranslational modifications of ion channels that contribute to the depolarization of sensory neurons (see Richardson and Vasko, 2002). These inflammatory mediators enhance kinase activity, resulting in the phosphorylation and modulation of ion channels to alter neuronal sensitivity. Peripheral sensitization is a key component of inflammatory diseases and chronic pain syndromes. This sensitization manifests as hyperalgesia and allodynia in humans and as hypernociception in animal models of pain. Although acute hypersensitivity after injury is an important component of the inflammatory response that aids in protecting the injury, there is oftentimes a maintenance of this hypersensitivity beyond the time required for tissue repair.

In addition to the widely studied effects of inflammatory mediators on kinase activity, there is an increase in the production of reactive oxygen (ROS) and nitrogen species (RNS) during inflammation and in animal models of chronic neuropathic pain (Bauerova and Bezek, 1999, Babior, 2000, Kim et al., 2004, Remans et al., 2005, Fidanboylu et al., 2011, Salvemini et al., 2011). This maintained sensitivity underlies many persistent inflammatory and chronic pain conditions, which are difficult to treat with current therapies. In particular, several studies have suggested a reversal of neuronal sensitivity with antioxidants (Khattab, 2006, Keeble et al., 2009, Fidanboylu et al., 2011, Duggett et al., 2016), yet there are deleterious effects of global antioxidant treatment due to the ubiquitous role of ROS/RNS in cellular signaling and cellular redox homeostasis (see Martin and Barrett, 2002). An important consequence of ROS/RNS production in sensory neurons is oxidative DNA damage. Indeed, previous studies demonstrated that ROS/RNS and subsequent DNA damage mediate changes in neuronal sensitivity induced by cisplatin, oxaliplatin or ionizing radiation in cultures derived from dorsal root ganglia (Jiang et al., 2008a, Vasko et al., 2011, Kelley et al., 2014).

The repair of DNA damage is critical for the maintenance of neuronal homeostasis (Brooks, 2002, McMurray, 2005, Fishel et al., 2007a, Hetman et al., 2010), as endogenous metabolic activity, oxidative stress secondary to injury (Kruman and Schwartz, 2008), environmental toxins, (Kisby et al., 1999) and drugs (Ahles and Saykin, 2007) all can cause neuronal DNA damage. Neurons contain the major DNA repair pathways including base excision repair (BER), nucleotide excision repair, mismatch repair, direct damage repair, and nonhomologous end-joining or homologous recombination (Fishel et al., 2007b, Barzilai et al., 2008, Fortini and Dogliotti, 2010). The BER pathway repairs DNA damage in the nucleus and mitochondria, caused by oxidative damage to bases, alkylation of bases, or deamination, and is likely the most important repair pathway for protecting neurons. The first step in BER is removal of the incorrect or damaged base by a DNA glycosylase. The second step in the BER pathway involves the enzyme APE1, which hydrolyzes the phosphodiester backbone immediately 5' to an apurinic/apyrimidinic (AP) site. This generates a normal 3'-hydroxyl group and an abasic deoxyribose-5-phosphate, which is processed by subsequent enzymes of the BER pathway.

As current therapies have limited efficacy and can result in significant side effects, determining the mechanisms for maintaining peripheral sensitization and using that information to design new therapies for treating inflammatory and chronic pain is clinically significant. Accordingly, the present disclosure provides insight into the pathway by which inflammatory mediators sustain changes in neuronal sensitivity and highlights the enhancement of neuronal DNA repair as a pharmacological target to alleviate inflammatory and/or chronic pain. Further, the present disclosure provides a compound, APX3330, to enhance DNA repair and reduce neuronal sensitivity.

BRIEF DESCRIPTION

The present disclosure relates generally to methods of reducing neuronal sensitivity, thereby reducing inflammatory and chronic pain. Particularly, it has been found herein that by enhancing the DNA base excision repair (BER) pathway, through the administration of APX3330 (and/or analogs thereof), neuronal sensitivity to inflammatory mediators is reduced, thereby alleviating inflammatory or chronic pain.

Based on the foregoing, in one aspect, the present disclosure is directed to a method of reducing neuronal sensitivity in a subject in need thereof. The method comprises administering to the subject an effective amount of an apurinic/apyrimidinic endonuclease 1 redox factor 1 (APE 1/Ref-1) inhibitor, pharmaceutically acceptable salts or pharmaceutically acceptable solvates thereof, which selectively inhibits the amino terminal portion of APE 1.

In another aspect, the present disclosure is directed to a method of treating inflammation and chronic pain in a subject suffering from diabetes. The method comprises administering to the subject an effective amount of an apurinic/apyrimidinic endonuclease 1 redox factor 1 (APE 1/Ref-1) inhibitor, pharmaceutically acceptable salts or pharmaceutically acceptable solvates thereof, which selectively inhibits the amino terminal portion of APE 1.

In yet another aspect, the present disclosure is directed to a method of enhancing neuronal DNA repair function in a subject suffering from diabetes. The method comprises administering to the subject an effective amount of an apurinic/apyrimidinic endonuclease 1 redox factor 1 (APE 1/Ref-1) inhibitor, pharmaceutically acceptable salts or pharmaceutically acceptable solvates thereof, which selectively inhibits the amino terminal portion of APE 1.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A is a representative western blot of pH2A.X and vinculin (loading control) expression in contralateral and ipsilateral L4/L5 DRG 5 days following unilateral CFA injection into the rat hindpaw. FIG. 1B depicts the mean±SEM of the density of pH2A.X from 6 experiments normalized to the amount of vinculin. An * indicates a statistically significant increase in the DRG ipsilateral to CFA injection compared to those contralateral to the injection ($p<0.05$, t-test). FIG. 1C are photomicrographs (20×) of pH2A.X in L5 DRG from a rat 5 days after CFA injection. Green fluorescence indicates the immunoreactivity to pH2A.X.

FIG. 2A are representative western blots for pH2A.X and vinculin (loading control) from cultures grown in the absence or presence of LPS or MCP-1 for the indicated time periods. FIG. 2B shows the mean±SEM of pH2A.X band density normalized to that of vinculin following treatment with 1 μg/ml LPS (light bars) or 100 ng/ml MCP-1 (dark bars). An * indicates a significant difference from expression at time=0, one-way ANOVA with Dunnett's posttest, $p<0.05$.

FIG. 5A shows the treatment schema. FIG. 5B are representative western blots for pH2A.X, APE1, HA tag and vinculin (loading control) from cultures grown in the absence or presence of LPS for 24 hours following the indicated pretreatments. FIG. 5C depicts pH2A.X densitometry. Each column represents the mean±SEM of pH2A.X band density normalized to that of vinculin induced by treatment with 3 μg/ml LPS following the indicated pretreatments in conjunction with SCsiRNA (light bars) or APE1siRNA (dark bars). An * indicates a significant difference from expression compared to SCsiRNA-treated vector control, two-way ANOVA with Dunnett's multiple comparisons posttest, $p<0.05$. FIG. 5D depicts CGRP release. Each column represents the mean±SEM of CGRP release (expressed as % of total content) stimulated by capsaicin following treatment with 3 μg/ml LPS in the absence and presence of APE1 overexpression, as indicated, in conjunction with SCsiRNA (light bars) or APE1siRNA (dark bars). An * indicates a significant difference in release compared to SCsiRNA-treated vector control, two-way ANOVA with Dunnett's multiple comparisons posttest, $p<0.05$.

FIG. 6A depicts the treatment schema. FIG. 6B are representative western blots for pH2A.X., APE1, HA tag and vinculin (loading control) from cultures grown in the absence or presence of MCP-1 for 24 hours following the indicated pretreatments. FIG. 6C depicts pH2A.X densitometry. Each column represents the mean±SEM of pH2A.X band density normalized to that of vinculin induced by treatment with 3 μg/ml MCP-1 following the indicated pretreatments in conjunction with SCsiRNA (light bars) or APE1siRNA (dark bars). An * indicates a significant difference from expression compared to SCsiRNA-treated vector control, two-way ANOVA with Dunnett's multiple comparisons posttest, $p<0.05$. FIG. 5D depicts CGRP release. Each column represents the mean±SEM of CGRP release (expressed as % of total content) stimulated by capsaicin following treatment with 3 μg/ml MCP-1 in the absence and presence of APE1 overexpression, as indicated, in conjunction with SCsiRNA (light bars) or APE1siRNA (dark bars). An * indicates a significant difference in release compared to SCsiRNA-treated vector control, two-way ANOVA with Dunnett's multiple comparisons posttest, $p<0.05$.

FIG. 7A shows that, in tumor cells, Ref-1/APE1 redox inhibition has multiple downstream effects on tumor growth, survival, migration and tumor inflammation. FIG. 7B shows that, in sensory neuron cells such as DRG neurons, the addition of APX3330 does not have a negative effect on the cells and promotes survival and functional protection through enhancement of Ref-1/APE1 DNA repair activity against oxidative DNA damaging agents (e.g. cisplatin, oxaliplatin) that invoked the DNA BER pathway. In the lower right panel, APX3330 attenuated neurotoxicity induced by systemic administration of cisplatin to tumor-bearing mice. FIG. 7C provides the treatment paradigm for investigation of the effects of cisplatin and APX3330 on DNA damage within DRG. FIG. 7D are representative blots demonstrating pH2A.X immunoreactivity at D24 and D31. FIG. 7E depicts the quantification of pH2A.X immunoreactivity. An * indicates statistical significance between D18 and D24 (FIG. 7E) as determined by a one-way ANOVA with Tukey's posttest with p<0.05. A † indicates statistical significance between Veh/Veh group and the Veh/Cis group (FIG. 7E) as determined by a two-way ANOVA with Bonferroni's posttest with p<0.05.

FIG. 8A is a schematic of E3330 and new compounds. Groups that were investigated include the Quinone series (A), 3-Position series (B), Alkyl sidechain series (C), and Carboxylic Acid/Amine series (D). FIG. 8B depicts current new analogs with more potent Ref-1 redox inhibition.

FIG. 9A depicts results from redox inhibition assays of APX3330 and its chemical analogues. FIG. 9B depicts the inhibition of $NF_\kappa B$ binding of APX3330 and its chemical analogues. FIG. 9C depicts the tumor cell killing ability of APX3330 and its analogues in a IMR32 cell line. FIG. 9D depicts the tumor cell killing ability of APX3330 and its analogues in a SK—N—SH cell line.

FIG. 10 depicts EMSA and transactivation data of APX3330 and its chemical analogues.

FIGS. 11A & 11B depicts the pharmacokinetic profile of APX2009 in IMR32 cells (FIG. 11A) and in SK—N—SH cells (FIG. 11B).

FIG. 12A depicts survival of cells from cultures treated with various concentrations of drugs as indicated for 24 hours. Each column represents the mean±SEM of percent. Cell viability as measured by trypan blue exclusion was determined on day 14 in culture from 3 independent harvests. An * indicates significant difference in survival in after drug treatment compared to no drug treatment using ANOVA and Tukey's post hoc test. FIG. 12B depicts neuronal cultures exposed to vehicle (DMSO) or to 20 µM of E3330, APX2007, APX2009 or APX2032 APX drugs (as indicated) for 72 hours and to various concentrations of cisplatin for 24 hours. Each column represents the mean±SEM of the percent survival of cells as measured by trypan blue exclusion. An * indicates significant difference in cultures not treated with cisplatin compared to cultures treated with the drug using ANOVA and Tukey's post hoc test.

FIG. 14A depicts cultures exposed to medium or to 10 or 20 µM of the various drugs (as indicated) for 72 hours prior to release experiments. FIG. 14B depicts cultures exposed to medium or to 10 or 20 µM of the various drugs (as indicated) for 72 hours and to cisplatin for 24 hours prior to release experiments. An * indicates a significant difference in capsaicin-stimulated release compared to untreated cells using ANOVA and Tukey's post hoc test.

FIG. 16A shows percent cells surviving after a 24 hour exposure to various concentrations of oxaliplatin. Each column represents the mean±SEM of percent cells surviving as measured by trypan blue exclusion after a 24 hour exposure to various concentrations of oxaliplatin as indicated. Cultures are treated for 72 hours with DMSO as a vehicle control (left) 10 µM APX2009 (center) or 20 µM APX2009 (right). FIG. 16B depicts basal release of CGRP (open columns) or release stimulated by 30 nM capsaicin (shaded columns) in fmol/well/min. Columns represent the mean±SEM of the basal release of CGRP (open columns) or release stimulated by 30 nM capsaicin (shaded columns) in fmol/well/min. The horizontal bar indicates cultures exposed to 30 µM oxaliplatin for 24 hours and 10 or 20 µM APX2009 for 72 hours prior to release experiments. FIG. 16C, the top panel shows representative Western blots of phospho-H2AX (pH2AX) and vinculin from cultures prior to and after 24 and 48 hours of exposure to 30 µM oxaliplatin and DMSO or 20 µM APX2009 for 72 hours before and during cisplatin treatment as indicated. The bottom panel represents the mean±SEM of the densitometry of pH2AX expression normalized to vinculin from 3 independent experiments. An * indicates a statistically significant difference on oxaliplatin treated cultures compared to controls using ANOVA and Tukey's post hoc test.

FIGS. 17A & 17B depicts Pa03C (tumor cells (transduced with TdTomato) grown in 3D cultures in the presence and absence of CAFs (transduced with EGFP). Tumor cells alone and tumor cells with CAFs in spheroids are shown. The middle and right quantitation graphs in FIGS. 17A & 17B show the tumor (middle) vs. CAF (right) intensity (FIG. 17A) and area (FIG. 17B). Spheroids were treated with APX2009 and the area of intensity (FIG. 17A) and area (FIG. 17B) of tumor (red channel) and CAF (green channel) were quantified following 12 days in culture. Representative images are shown in FIG. 17C. Differences were determined using both Student's t test (vehicle control vs drug treatment at each dose) and one-way ANOVA and statistical differences were observed for the tumor alone or tumor co-cultured with CAFs (*p<0.05,  p<0.01, *p<0.001). No differences were observed in CAFs treated with APX2009 from control.

DETAILED DESCRIPTION

Figure 1A:
FIGS. 1A-1C shows that DNA damage is enhanced in the lumbar DRG following hindpaw inflammation.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure relates generally to methods of reducing neuronal sensitivity, thereby reducing inflammation and chronic pain. Particularly, it has been found herein that by enhancing the DNA base excision repair (BER) pathway, through the administration of APX3330, neuronal sensitivity to inflammatory mediators is reduced, thereby alleviating inflammatory or chronic pain.

In suitable embodiments, the present disclosure includes administering to a subject in need thereof an effective amount of an APE1 inhibitor, pharmaceutically acceptable salts or pharmaceutically acceptable solvates thereof, the APE1 inhibitor capable of interacting with the APE1 protein such to cause unfolding of the APE1 protein, inhibiting the ability of APE1 to interact with other proteins in the neurons or to perform its redox signaling function. In particular suitable embodiments, the APE1 inhibitor is 3 [5 (2,3-dimethoxy-6-methyl-1,4-benzoquinoyl)]-2-nonyl-2-propenoic acid], (hereinafter "E3330" or "3330" or "APX3330"), and/or its analogs (e.g., [(2E)-2-[(3-methoxy-1,4-dioxo-1,4-dihydronaphthalen-2-yl)methylidene]-N,N-diethylpentanamide] (hereinafter "APX2009"), (2E)-2-[(3-methoxy-1,4-dioxo-1,4-dihydronapthalen-2-yl)methylidene]-N,N-dimethylpentanamide] (hereinafter "APX2007"), (2E)-2-[(3-methoxy-1,4-dioxo-1,4-dihydronapthalen-2-yl)methylidene]-N-methoxypentanamide] (hereinafter "APX2014"), (2E)-2-(3-methoxy-1,4-dioxo-1,4-dihydronaphthalen-2-yl)-N,N,2-trimethylprop-2-enamide (hereinafter "APX2032")). Additional suitable analogs are shown below. Further information on APX3330 may be found in Abe et al., U.S. Pat. No. 5,210,239, and information on APX2009 may be found in Kelley et al., J Pharmacol Exp Ther. 2016 November, 359(2): 300-309, each incorporated herein by reference to the extent they are consistent herewith.

APX3330

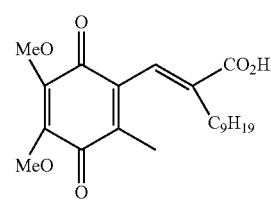

APX2009

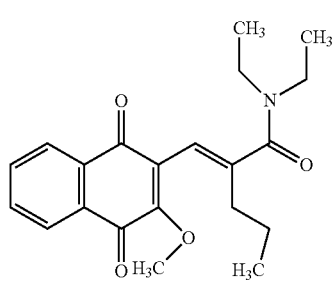

APX2014

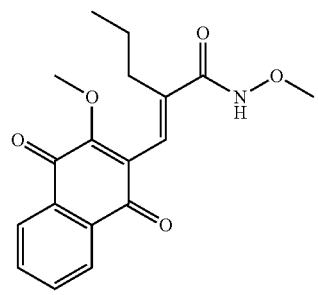

APX2007

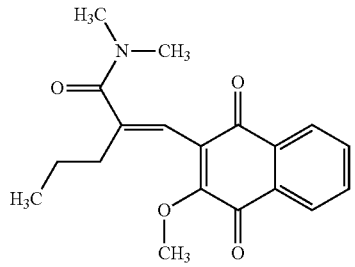

APX2032

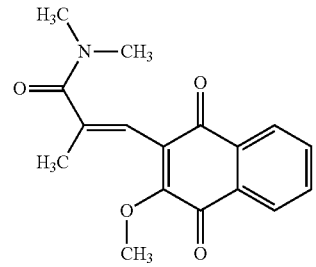

It has herein been found that the administration of APX3330 (and/or its analogs) inhibits APE1 protein from interacting with other proteins in the neurons. This interaction inhibition allows for APE1 to be free to perform enhanced DNA repair functions at an oxidized or abasic site in damaged DNA (damaged by inflammatory and other effectors of neuronal pain pathway induction). Particularly, as described in the Example below, it was first demonstrated that peripheral inflammation induces DNA damage in the soma of neurons of the lumbar DRG and recapitulates this DNA damage in DRG cultures exposed to the inflammatory mediators, LPS or MCP-1. It is also established herein that DNA damage mediates changes in neuronal sensitivity, as determined by capsaicin-stimulated neuropeptide release by exogenously enhancing DNA repair via the overexpression of the enzyme APE1. The present disclosure thereby identifies a pathway by which inflammatory mediators sustain changes in neuronal sensitivity and highlights the enhancement of neuronal DNA repair as a pharmacological target to alleviate inflammatory or chronic pain.

In one particular embodiment, the administration of APX3330 (and/or its analogs) can help to prevent or reduce the effects of chemotherapy-induced peripheral neuropathy (CIPN). Chemotherapy-induced peripheral neuropathy (CIPN) is a potentially debilitating side effect of a number of chemotherapeutic agents. The major symptoms of these neuropathies, including allodynia, increased sensitivity to cold, loss of proprioception, loss of touch, reduced tendon reflexes and pain, are largely characterized by alterations in peripheral sensory function, suggesting that sensory neurons are a major target of the toxicity.

Suitable dosages of the APE1 inhibitor, pharmaceutically acceptable salts or pharmaceutically acceptable solvates thereof, for use in the methods of the present disclosure will depend upon a number of factors including, for example, age and weight of an individual, severity of inflammatory or chronic pain, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

In one particularly suitable embodiment, the APE1/Ref-1 inhibitor is APX3330, and the subject is administered from about 5 µM to about 50 µM APX3330.

In some embodiments, the APE1 inhibitor is administered via a composition that includes the APE1 inhibitor and a pharmaceutically acceptable carrier. Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (e.g., APX3330) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein. For example, in one embodiment, the APE1 inhibitor can be administered with one or more of platinum drugs (e.g., cisplatin, oxaliplatin carboplatin), taxanes (e.g., paclitaxel, docetaxel, cabazitaxel), doxorubicin, alkaloids (e.g., vincristine, vinblastine, etoposide) thalidomide, lenolidomide, pomalidomide, bortexomib, carfilzomib, eribulin, or ionizing radiation.

The pharmaceutical compositions including the APE1 inhibitor and/or pharmaceutical carriers used in the methods of the present disclosure can be administered to a subset of individuals in need. As used herein, an "individual in need" refers to an individual at risk for or having inflammatory and/or chronic pain, or an individual at risk for or having a disease or disorder associated with inflammation and/or chronic pain (e.g., obesity, diabetes, asthma, arthritis (osteoarthritis, rheumatoid arthritis, psoriatic arthritis) chronic periodontitis, ulcerative colitis, Crohn's disease, chronic sinusitis, chronic active hepatitis, chronic peptic ulcer, diverticulitis, fibromyalgia, irritable bowel syndrome, Alzheimer's, Parkinson's disease, atherosclerosis, and tuberculosis). Additionally, an "individual in need" is also used herein to refer to an individual at risk for or diagnosed by a medical professional as having inflammatory or chronic pain. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Various functions and advantages of these and other embodiments of the present disclosure will be more fully understood from the examples shown below. The examples are intended to illustrate the benefits of the present disclosure, but do not exemplify the full scope of the disclosure.

EXAMPLE 1

In this Example, the dependency of persistent changes in the sensitivity of sensory neurons secondary to exposure to inflammatory mediates on DNA damage was analyzed. Further, the effects of enhancing the DNA BER pathway on DNA damage and neuronal sensitivity were analyzed.

Materials and Methods

Unless otherwise specified, tissue culture supplies were obtained from Thermo Fisher Scientific (Waltham, Mass.). Poly-D-lysine, laminin, mouse monoclonal anti-vinculin antibody, 1-methyl-2-pyrrolidone (MPL), complete Freund's adjuvant (CFA), and routine chemicals were purchased from Sigma-Aldrich (St. Louis, Mo.). Nerve growth factor was purchased from Envigo (Indianapolis, Ind.) and Normocin from Invivogen (San Diego, Calif.). Neuroporter was purchased from Genlantis (San Diego, Calif.). Mouse monoclonal antihuman APE1 antibodies were raised in the laboratory and available from Novus Biologicals (Littleton, Colo.), mouse monoclonal anti-phospho-H2AX antibody was from EMD Millipore (Billerica, Mass.), and anti-Hemagglutinin (HA) antibody conjugated to horseradish peroxidase was purchased from Miltenyi Biotec (San Diego, Calif.). Chemiluminescence secondary antibodies were obtained from Roche Diagnostics Corp. (Indianapolis, Ind.).

APX3330 (also referred to herein as "E3330") was synthesized per previous publications (e.g., J Med Chem. 2010 Feb. 11; 53(3): 1200-1210), dissolved in N,N-dimethylformamide (Sigma-Aldrich) and stored as a 40 mM stock at −80° C. Lipopolysaccharides (LPS) from *Escherichia coli* 0111:B4 was purchased from Sigma-Aldrich Inc. (St. Louis, Mo.), dissolved in MPL and stored as a 50 mM at −20° C. for a month. Recombinant rat CCL2/MCP-1 protein was purchased from R&D Systems (Minneapolis, Minn.), dissolved in PBS and stored at −20° C. for up to a month. The TLR4 antagonist, LPS-RS, was purchased from Invivogen, dissolved in MPL and stored at −80° C. The CCR2 antagonist, RS 504393, was purchased from Sigma-Aldrich Inc. (St. Louis, Mo.), dissolved in MPL and stored −20° C. for a month. Before drug treatment, the stocks were diluted in F-12 growth medium and added to cultures and incubated for 2-96 hours as indicated. The Animal Care and Use Committee at Indiana University School of Medicine, Indianapolis, Ind, approved all procedures used in this Example.

Hindpaw Inflammation

Rats were anesthetized briefly with isoflurane and injected subcutaneously with 150 µl of a 1:1 (v/v) solution of CFA and 0.9% saline into the plantar surface of the right hind paw. Inflammation was confirmed by redness and swelling; only animals with an increase in the injected paw thickness of 3.5 mm or greater were used in experiments.

Cell Culture

Dorsal root ganglia (DRG) were dissected from all spinal levels of adult male (150-175 g) Sprague-Dawley rats (Envigo, Indianapolis, Ind.) and the cells were dissociated as previously described (Kelley et al., 2014). Briefly, the rats were euthanized by $CO_2$ asphyxiation. DRGs were transferred into collagenase solution (1 mg/ml) and incubated for 1 hour at 37° C. The digested DRGs were then rinsed with growth medium, centrifuged and dissociated by mechanical agitation. Approximately 30,000 cells were plated into each well of 12-well culture plates. All culture dishes were precoated with poly-D-lysine and laminin. Cells were maintained in F-12 media supplemented with 10% horse serum, 2 mM glutamine, 100 µg/ml Normocin, 50 µg/ml penicillin, 50 µg/ml streptomycin, 50 µM 5-fluoro-2'-deoxyuridine, 150 µM uridine, and 30 ng/ml of NGF in 3% $CO_2$ at 37° C. Growth medium was changed every other day.

Modulation of APE1 Expression

Small interfering RNAs to APE1 (APE1siRNA) and scrambled siRNA (SCsiRNA) controls were used to decrease APE1 protein expression in sensory neuronal cell cultures and as controls, respectively, as described previously (Vasko et al., 2005, Jiang et al., 2008a). On day 3 in culture, the growth media was replaced with 0.5 ml of Opti-MEM 1 media containing 100 nM of APE1siRNA (5'-GUCUGGUAAGACUGGAGUACC-3' (SEQ ID NO:1)) or SCsiRNA (5'-CCAUGAGGUCAGCAUGGU-CUG-3'(SEQ ID NO:2)); (Vasko et al., 2005)) and 10 µl of the transfecting reagent, Neuroporter. On the next day, 0.5 ml of the growth media without antibiotics was added to each well, and after an additional 24 hours the media containing siRNA was replaced with normal growth media. Lentiviral constructs containing (1) the CMV promoter, HA-tagged APE1, IRES, and enhanced green fluorescent protein (EGFP); or (2) CMV, IRES, and EGFP were developed. DNA sequencing confirmed the constructs in the pLenti6-R4R2-V5 plasmid containing WT-, C65-, or 226+ 177-APE1-IRES-EGFP. For lentiviral infections, DRG cells were cultured 5 days before 150 pfu/cell of the lentivirus was added to the media. Two days later, the virus was removed and the cells grown an additional 5 days in regular media. In this Example, APE1 expression was selectively reduced in the neuronal cultures with siRNA to rat APE1 mRNA and added back human APE1 transgenes that are not affected by the rat siRNA since the human APE1 homolog has a different nucleic acid sequence at the binding site (Vasko et al., 2005).

Immunoblotting

Tissues or cells were harvested, lysed in RIPA buffer (Santa Cruz Biotechnology; Santa Cruz, Calif., USA), sonicated, and cleared of cellular debris by centrifuging at 4000 RPM for 2 minutes. Protein was quantified using Lowry assay, and electrophoresed in a 12% SDS-polyacrylamide gel. After electrophoresis, proteins were transferred to a PVDF membrane, and blocked with Tris-buffered saline containing 0.1% Tween-20 (TBST) and 5% nonfat dry milk for 1 hour at room temperature while gently agitating.

Mouse monoclonal antihuman Ape1 antibodies (1:1000), mouse monoclonal anti-phospho H2AX antibodies (1:1000), mouse monoclonal anti-vinculin antibody (1:1000), and anti-Hemagglutinin (HA) antibody were added to the blocking solution and incubated for 2 hours at room temperature while gently agitating. Antibody binding was detected following appropriate secondary antibody methods using chemiluminescence. The density of the bands was measured using Quantity One software from Bio-Rad (Hercules, Calif.) and data expressed as density normalized to vinculin.

Measurement of CGRP Release

After neuronal cultures were treated with the appropriate drugs, the cultures were washed once with HEPES buffer consisting of (in mM) 25 HEPES, 135 NaCl, 3.5 KCl, 2.5 $CaCl_2$, 1 $MgCl_2$, 3.3 D-glucose, and 0.1% bovine serum albumin, pH 7.4 and maintained at 37° C. They were then incubated for successive 10-minute intervals with 0.4 ml of HEPES buffer alone (basal release), with buffer containing 30 nM capsaicin, then with buffer alone (to assess return to basal release). After each incubation, the buffer was removed and the amount of immunoreactive CGRP in each sample was measured using radioimmunoassay as previously described (Chen et al., 1996). After the release experiment, the cells in each well were in 0.4 ml of 0.1 M HCl10 minutes and an aliquot taken to measure total CGRP content in the cultures using radioimmunoassay. Total content (fmol/well) was calculated by adding the total amount released in all incubations to the amount measured in the cells. The release data is calculated as fmol released/well/10 minutes.

Statistical Analysis

Data are expressed as the mean±SEM from at least three repeats of each experiment. Differences in pH2A.X expression and CGRP release in DRG cultures were determined using one- or two-way analysis of variance (ANOVA) and Dunnett's post hoc test. Differences in pH2A.X expression in DRG tissues were determined using Student t-tests. In all cases, significance was set at $p<0.05$) comparing treated versus controls.

Results

Hindpaw Inflammation Elicited DNA Damage in the L4/L5 DRG and Enhances the Expression of APE1

The ability of neurons to repair DNA is critically important in maintaining neuronal homeostasis (Brooks, 2002, McMurray, 2005, Fishel et al., 2007a, Hetman et al., 2010). The question remains, however, whether tissue inflammation produces DNA damage. To determine whether tissue inflammation elicits DNA damage, complete Freund's adjuvant (1:1 dilution of CFA: saline) was injected unilaterally into the plantar hindpaw of the rat. Five days following injection, the animals were sacrificed and the lumbar DRG were collected. In this manner, DNA damage and protein expression from tissue ipsilateral to the inflammation could be compared to the contralateral control. As can be seen in FIG. 1A, inflammation induced an increase in double-strand DNA breaks, as indicated by a 58% increase in the phosphorylation of H2A.X (Rogakou et al., 1998). To ascertain whether DNA damage occurred within the sensory neuronal soma in the DRG, immunohistochemistry was performed.

Figure 1B:
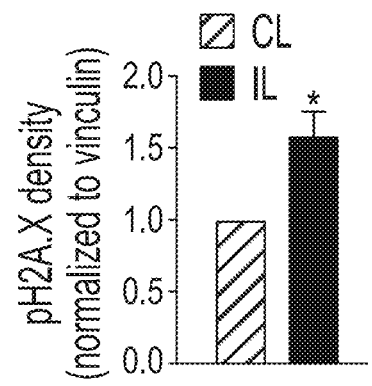
Figure 1C:
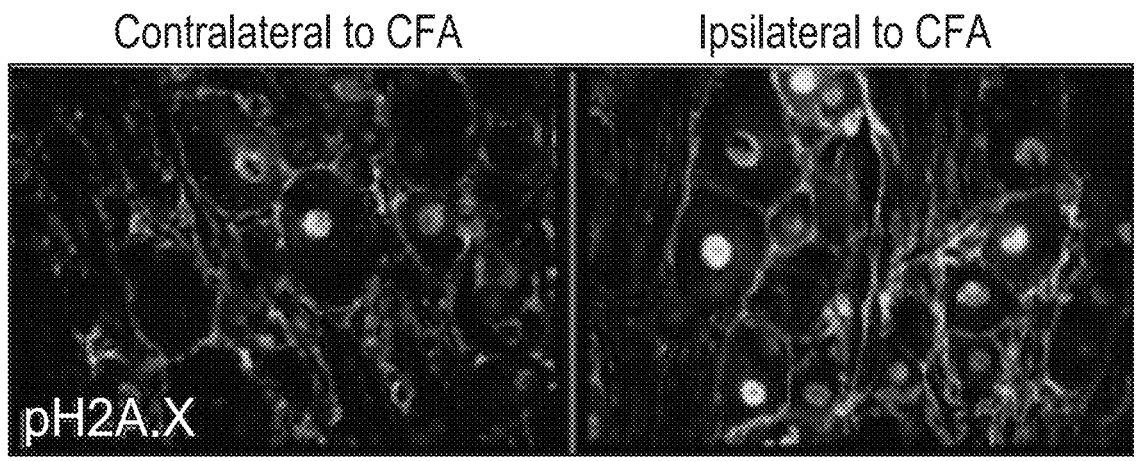

As illustrated in representative images in FIG. 1B, immunoreactivity for pH2A.X was localized to the nuclei of both neurons and supporting cells. The immunoreactivity was brighter in sensory neuronal soma derived from DRG ipsilateral to inflammation, validating the idea that inflammation causes DNA damage within the sensory neurons. The mechanisms by which inflammation causes DNA damage and the impact of the DNA damage on the sensitivity of sensory neurons are yet unknown.

The Inflammatory Mediators, LPS and MCP-1, Enhanced DNA Damage in a Time-Dependent Manner Injection of CFA into the hindpaw of a rat elicits behavioral hypersensitivity to thermal and mechanical stimuli (Stein et al., 1988, Woolf et al., 1994), and this hypersensitivity has been attributed to the enhancement of local inflammatory mediators within the damaged tissue (Ferreira et al., 1988, Williams and Higgs, 1988, Cunha et al., 1992, Ferreira et al., 1993, Safieh-Garabedian et al., 1995). To ascertain whether DNA damage mediates the change in neuronal sensitivity induced by inflammation, cultures of sensory neurons were utilized. In lieu of tissue inflammation, the cultures were exposed to LPS or MCP-1 and then DNA double-strand breaks and neuronal sensitivity were determined. In neuronal cultures, exposure to LPS (1 µg/ml) resulted in a time-dependent increase in the levels of pH2A.X, apparent within 16 hours of treatment and peaking at 24 hours. As observed with LPS treatment, exposure to MCP-1 (100 ng/ml) induced pH2A.X expression, with an onset of 16 hours and peak effects at 24 hours. Because the peak effects of the inflammatory mediators on DNA damage were observed at 24 hours, all subsequent experiments were performed at that timepoint.

LPS and MCP-1 Altered CGRP Release in a Concentration-Dependent Manner

Figure 3:
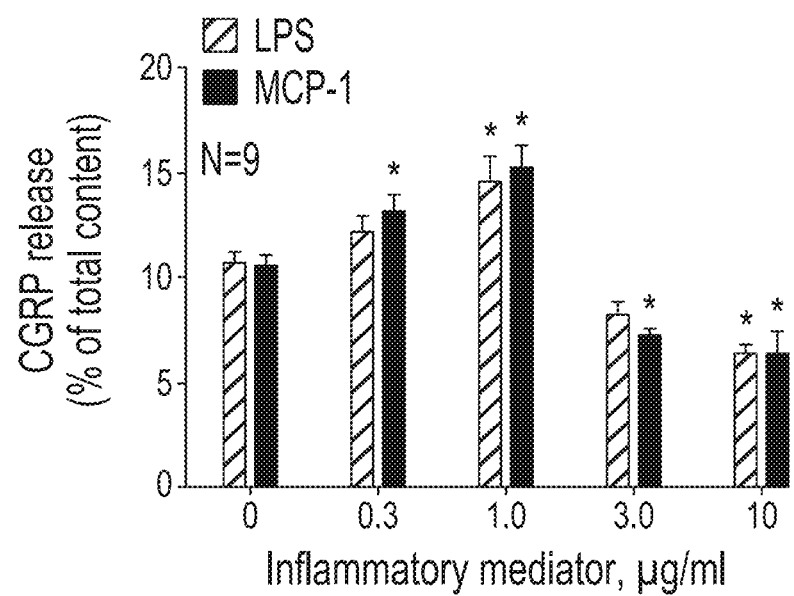
FIG. 3 depicts that the CGRP release from neuronal cultures was altered following exposure to inflammatory mediators. Columns represent the mean±SEM of CGRP release stimulated by a 10-minute exposure to 30 nM capsaicin following a 24-hour exposure to increasing concentrations of LPS (light bars) or MCP-1 (dark bars). An * indicates a significant difference from release in the absence of LPS or MCP-1, one-way ANOVA with Dunnett's posttest, $p<0.05$.

To demonstrate inflammatory mediator-induced changes in the sensitivity of neurons within DRG cultures, the cultures were exposed to increasing concentrations of each of the inflammatory mediators for 24 hours and then the basal and stimulated release of the putative nociceptive neuropeptide, calcitonin gene-related peptide, was examined. The release of CGRP was stimulated by capsaicin, an agonist of the TRPV1 receptor. As illustrated in FIG. 3, capsaicin stimulated the release of approximately 10% of the total content of CGRP over a 10-minute period. Exposing sensory neurons to a low concentration of LPS (1.0 µg/ml) enhanced the capsaicin-stimulated release of CGRP to 14.4±1.2% of total content. Similarly, exposure of cultures to low concentrations of MCP-1 for 24 hours augmented the release of CGRP to 13.0±0.8 and 15.0±1.0% of total content in cultures treated with 0.3 and 1.0 µg/ml MCP-1, respectively. In contrast, treatment with higher concentrations of the inflammatory mediators significantly decreased the release of CGRP to 6.3±0.4 and 6.3±1.0% of total content in cultures treated with 10.0 µg/ml LPS and MCP-1, respectively. The changes in release of CGRP were not secondary to an altered content of CGRP in the neurons, as the total content of CGRP was similar in cultures treated with vehicle, LPS, and MCP-1 (data not shown).

Figure 4A:
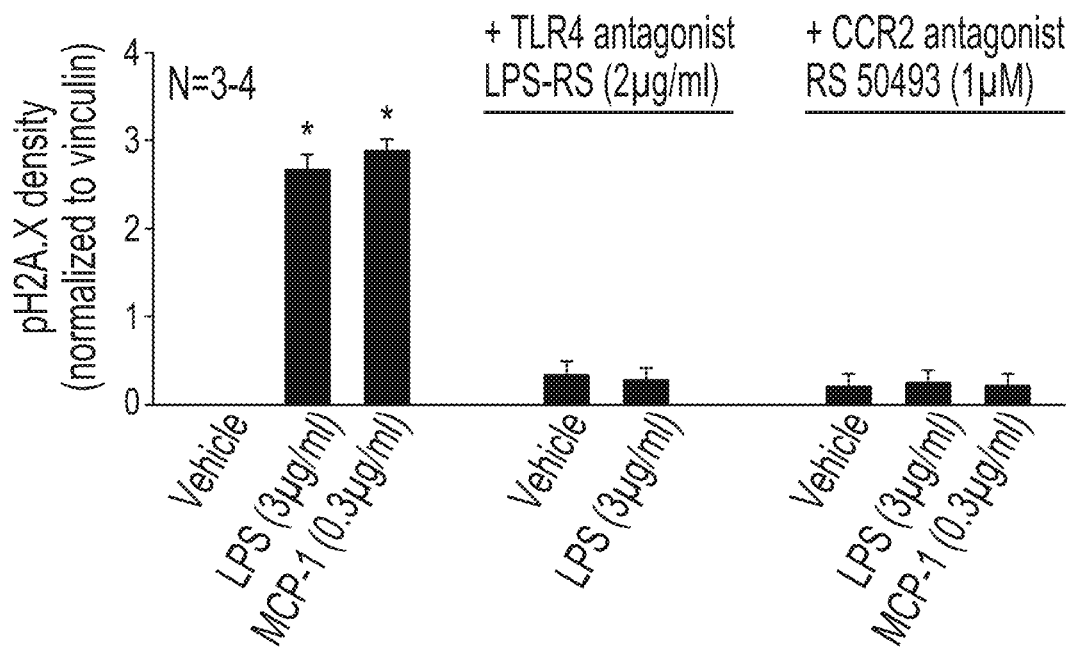
FIGS. 4A & 4B depict that the changes in DNA damage and stimulated CGRP release following exposure to LPS or MCP-1 were reversed by antagonists to the TLR4 (LPS) and CCR2 (MCP-1 and LPS). Columns represent the mean±SEM of pH2A.X expression (FIG. 4A) or CGRP release stimulated by a 10-minute exposure to 30 nM capsaicin (FIG. 4B) following a 24 hr exposure to 3 μg/ml LPS (light bars) or 0.3 μg/ml MCP-1 (dark bars) in the absence or presence of LPS-RS or RS 50493, as indicated. An * indicates a significant difference from DNA damage or release in the absence of LPS or MCP-1, one-way ANOVA with Dunnett's posttest, $p<0.05$.

The Effects of LPS and MCP-1 to Induce DNA Damage and Alter CGRP Release Were Reversed By Antagonists of the TLR4 and CCR2 Receptors The cognate receptor pathways that are activated by LPS and MCP-1 are the TLR4 receptor pathway and the CCR2 receptor pathway, respectively (Charo et al., 1994, Poltorak et al., 1998); however, there have been recent reports that these inflammatory agents may modulate other targets (Meseguer et al., 2014). Therefore, it was determined whether blocking the activation of the TLR4 and CCR2 inhibited the effects of the inflammatory mediators to enhance pH2A.X expression and alter neuronal sensitivity by performing experiments in the presence of the TLR4 antagonist, LPS-RS (2 µg/ml), or the CCR2 antagonist, RS 50493 (1 µM), respectively. In these experiments, DNA damage was induced with differing concentrations of the LPS and MCP-1. 3.0 µg/ml LPS was used to emulate a loss of function induced by the inflammatory mediators and 0.3 µg/ml MCP-1 was used to mimic the sensitization of neuropeptide release that correlates with DNA damage. Recent studies have demonstrated that LPS treatment of sensory neurons in culture can upregulate the endogenous production of CCL2 (Miller et al., 2015), therefore it was also examined whether the CCR2 antagonist would block the effects of LPS on neuronal DNA damage and neuropeptide release. The cultures were treated with the receptor antagonists 1 hour prior to the introduction of the inflammatory mediators and maintained in the media throughout the exposure. As previously observed, both LPS and MCP-1 treatment induced the expression of pH2A.X. The LPS-induced increase in expression was reversed by both the TLR4 antagonist (89.9% reduction) and by the CCR2 antagonist (92.5% reduction). The CCR2 antagonist also reduced the expression of pH2A.X to only 8.5% of the expression elicited by MCP-1 alone (FIG. 4A).

Figure 4B:
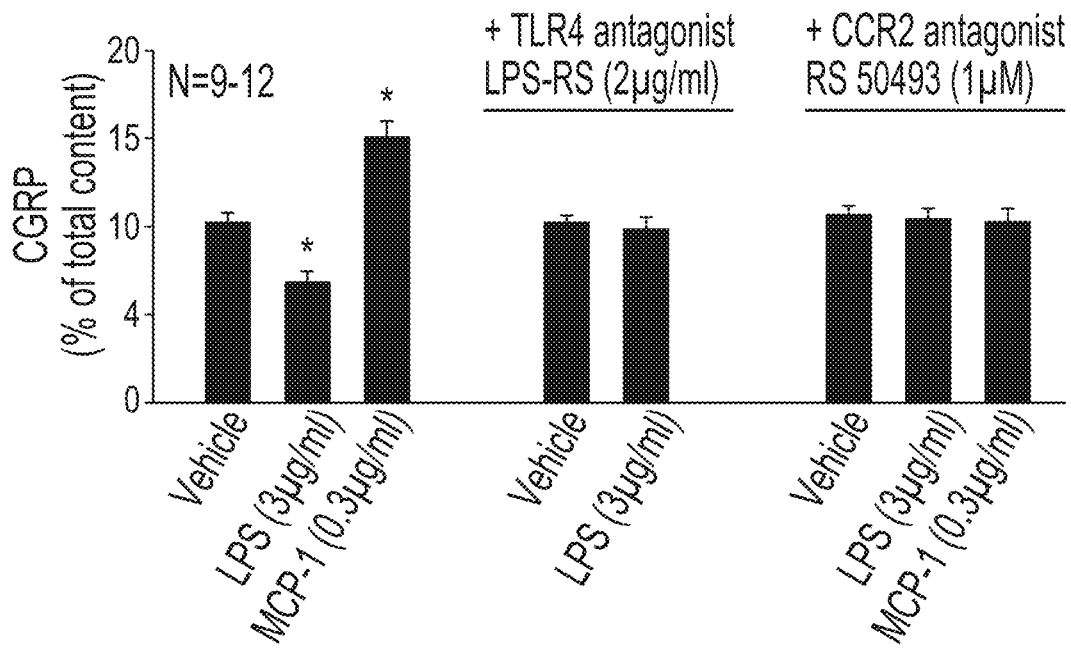

The effects of the antagonists to block inflammatory mediator-induced changes in neuropeptide release were also examined. As observed previously, 3.0 µg/ml LPS decreased the stimulated release of CGRP from neuronal cultures by 32.7%. Treatment with either the TLR4 or CCR2 antagonist blocked the decrease in release induced by LPS. Exposing neuronal cultures to 0.3 µg/ml MCP-1 for 24 hours elicited the sensitization of CGRP release to 142.8% of the release in the absence of MCP-1. This augmentation was prevented by treatment with RS 50493 (FIG. 4B).

The Effects of LPS to Induce DNA Damage and Attenuate CGRP Release Were Reversed By APE1 OE (wt or C65), But Not APE1 OE (226/177)

Neurons contain the major DNA repair pathways including BER, nucleotide excision repair, mismatch repair, direct damage repair, and nonhomologous end-joining or homologous recombination (Fishel et al., 2007b, Barzilai et al., 2008, Fortini and Dogliotti, 2010). The BER pathway repairs DNA damage in the nucleus and in mitochondria that is caused by oxidative damage to bases, alkylation of bases, or deamination and is likely the most important repair pathway for protecting neurons (see Fishel et al., 2007b). It was next examined whether enhancing or diminishing the activity of APE1, a critical enzyme in the BER pathway, altered the DNA damage and changes in neuronal sensitivity induced by LPS and MCP-1 treatment.

Figure 5A:
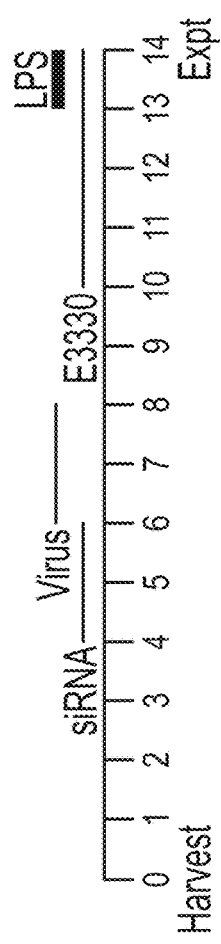
FIGS. 5A-5D depict that the effects of LPS to include DNA damage and inhibit CGRP release were reversed by increasing APE1-mediated DNA repair.
Figure 5B:
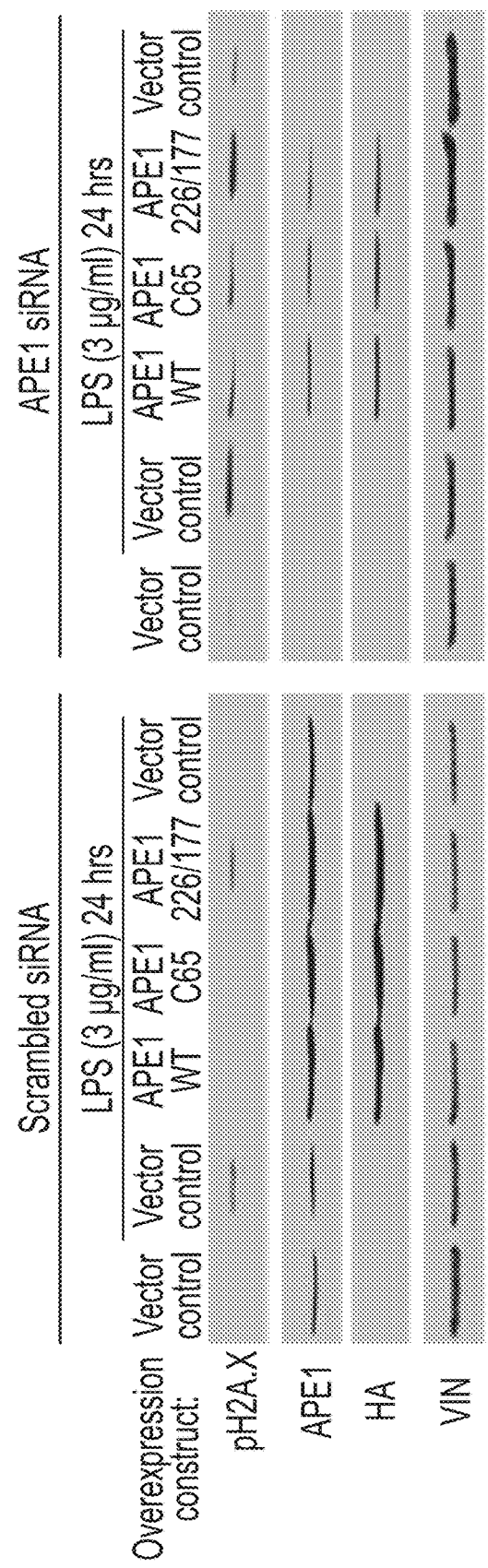
Figure 5C:
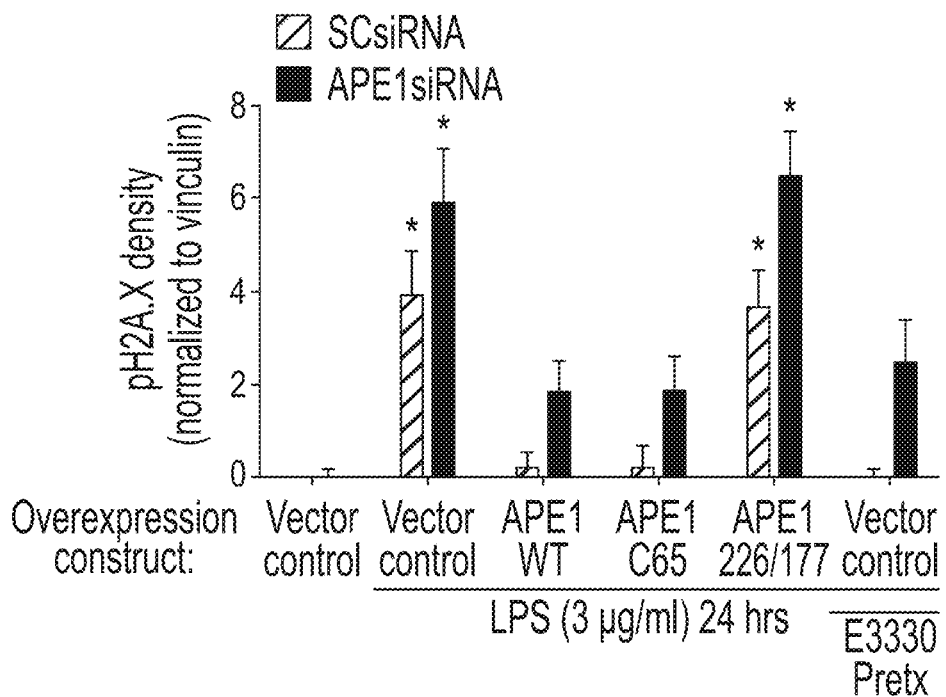
Figure 5D:
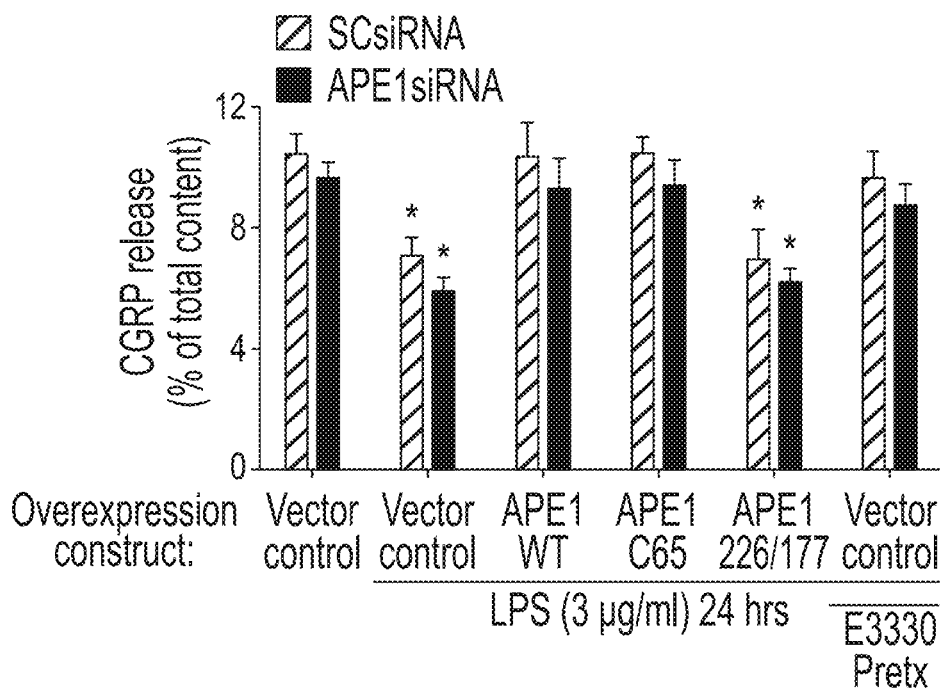

For this Example, cultures were treated as illustrated in FIG. 5A. Cultures were transfected with SCsiRNA or APE 1 siRNA on days 4-6 in culture and then exposed to lentivirus containing expression constructs for vector control, wildtype APE1, C65 APE1, or 226/117 APE1 on days 6-8 in culture. The C65 APE1 mutant has impaired redox function whereas the 226/117 APE1 mutant has impaired DNA repair function (Izumi et al., 2004, Luo et al., 2008). In one set of cultures, the neurons were treated with E3330 on days 10-14 days in culture. Finally, cultures were treated with LPS (3 µg/ml) for the 24 hours immediately prior to experiments. When cultures treated with SCsiRNA were exposed to LPS for 24 hours, there was a significant induction of pH2A.X expression (FIGS. 5B and 5C). Exogenous expression of either wildtype APE1 or C65 APE1 (repair-competent), at levels ~175% of wildtype endogenous expression and indicated by the novel expression of HA tag (FIG. 5B), ameliorated the ability of LPS to induce double-strand breaks, decreasing the density of pH2A.X by 95% and 94%, respectively. In contrast, exogenous expression of the 227/177 APE1 mutant (repair-deficient) had no effect on LPS-induced pH2A.X levels. Similar effects were observed in cultures treated with APE1siRNA, which decreased APE1 expression to ~20% of wildtype expression; LPS induced pH2A.X and this trended to be more extensive compared to the SCsiRNA-treated cultures. Interestingly, the enhancement of the DNA repair activity of APE1 by E3330 mimicked the effects of exogenously expressing wildtype APE1. Pretreatment with E3330 (20 µM) prevented the induction of pH2A.X in both SCsiRNA- and APE1siRNA-treated cultures. To discover whether a reversal in DNA damage also reversed the effects of LPS on neuronal sensitivity, the stimulated release of CGRP was also examined. LPS (3 µg/ml) treatment attenuated the release of CGRP stimulated by capsaicin (FIG. 5D). In cultures treated with SCsiRNA, the stimulated release of CGRP from vehicle-treated wells was 10.4±0.6% of total content, whereas release from cells treated with LPS for 24 hours was decreased to 7.1±0.6% of total content. Exogenous expression of either wildtype APE1 or C65 APE1 (repair-competent) reversed the effects of LPS, so that the stimulated release of CGRP was 10.4±1.1 and 10.5±0.4% of total content in the presence of APE1 wildtype and C65 mutant, respectively. Exogenous expression of the repair-deficient APE1 mutant did not reverse the effects of LPS, as release was still attenuated at 7.0±0.9% of total content. Finally, treatment with E3330 also protected against the effects of LPS on CGRP release; release following E3330 treatment was 9.7±0.8% of total content, which was no different than release in the absence of LPS treatment.

The Effects of MCP-1 to Induce DNA Damage and Alter CGRP Release Were Reversed By APE1 OE (wt or C65), But Not APE1 OE (226/177)

Figure 2A:
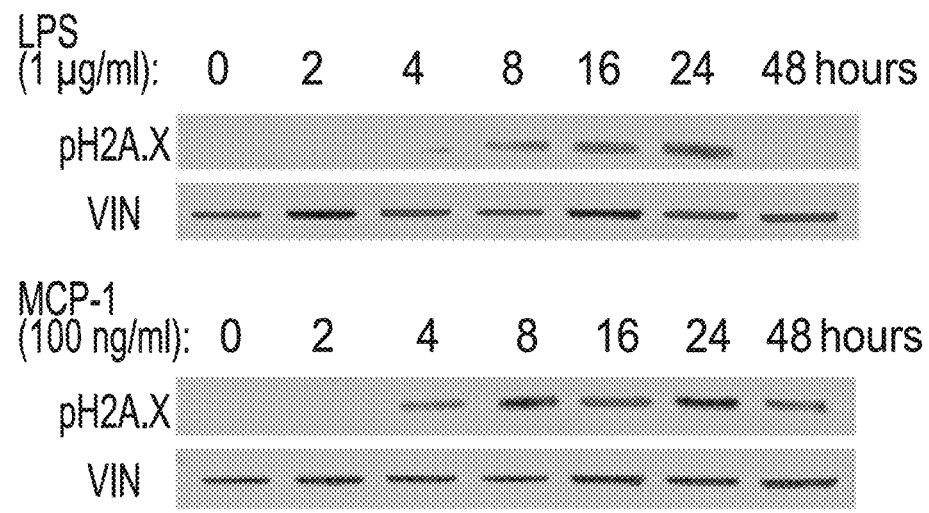
FIGS. 2A & 2B show that DNA damage is enhanced in neuronal cultures in a time-dependent manner following exposure to inflammatory mediators.
Figure 2B:
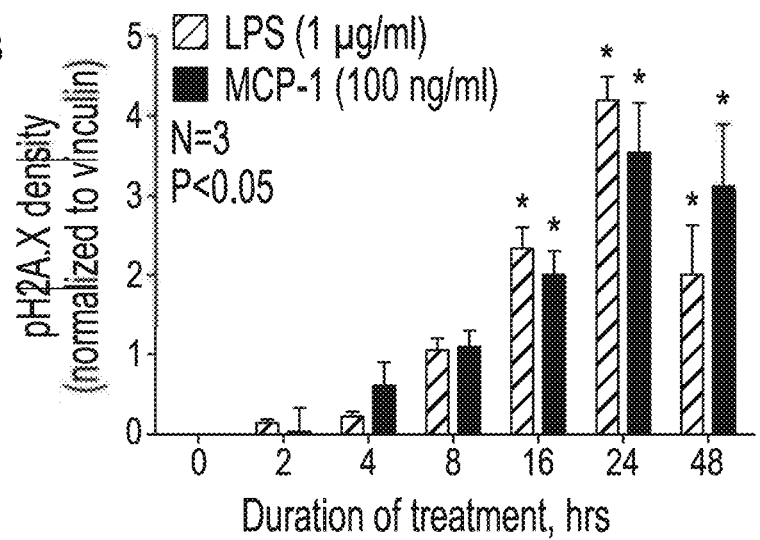
Figure 6A:
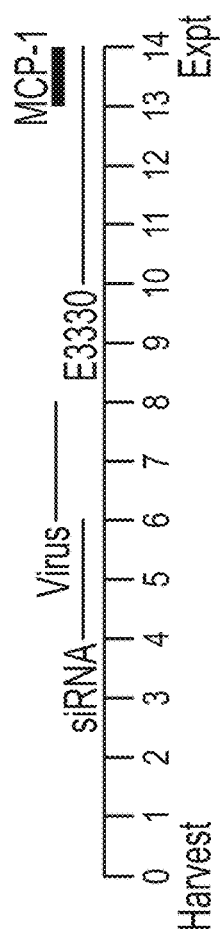
FIGS. 6A-6D depict that the effects of MCP-1 to induce DNA damage and augment CGRP release were reversed by increasing APE1-mediated DNA repair.
Figure 6B:
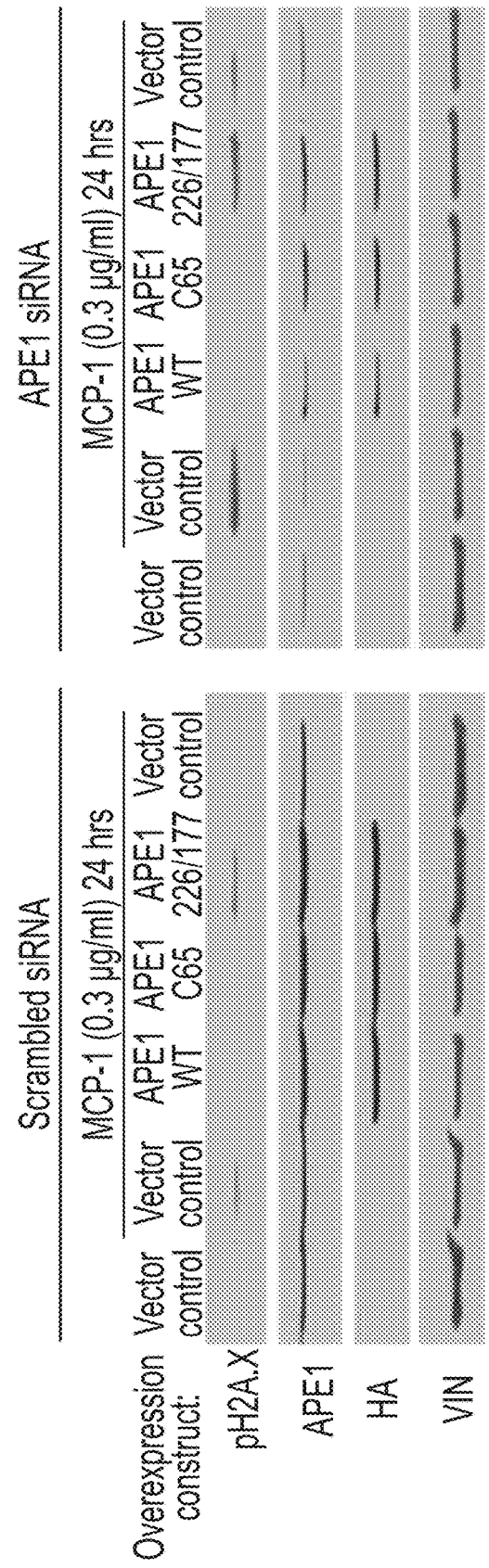
Figure 6C:
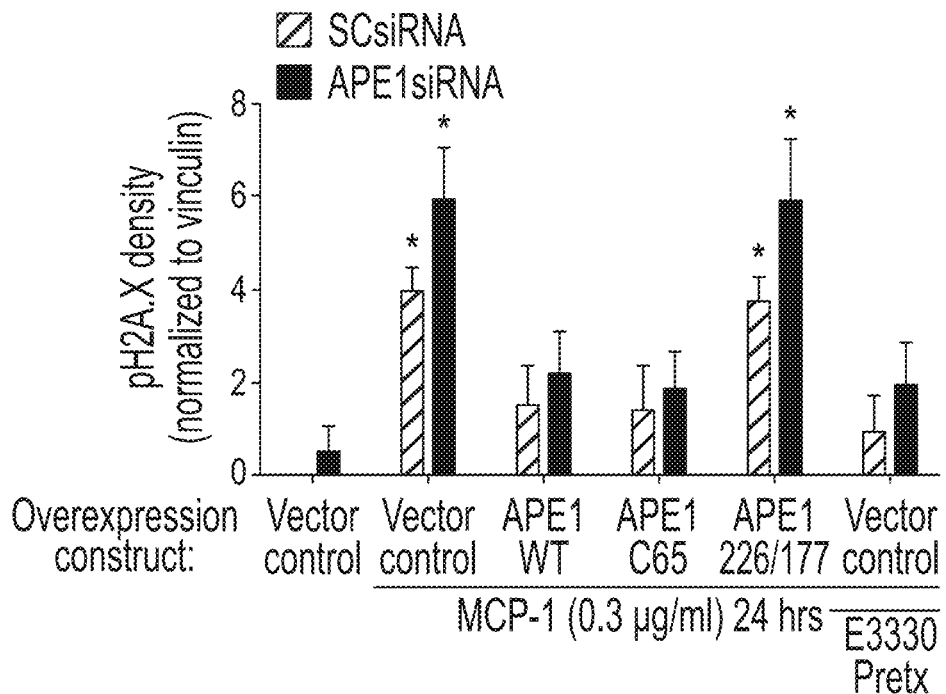
Figure 6D:
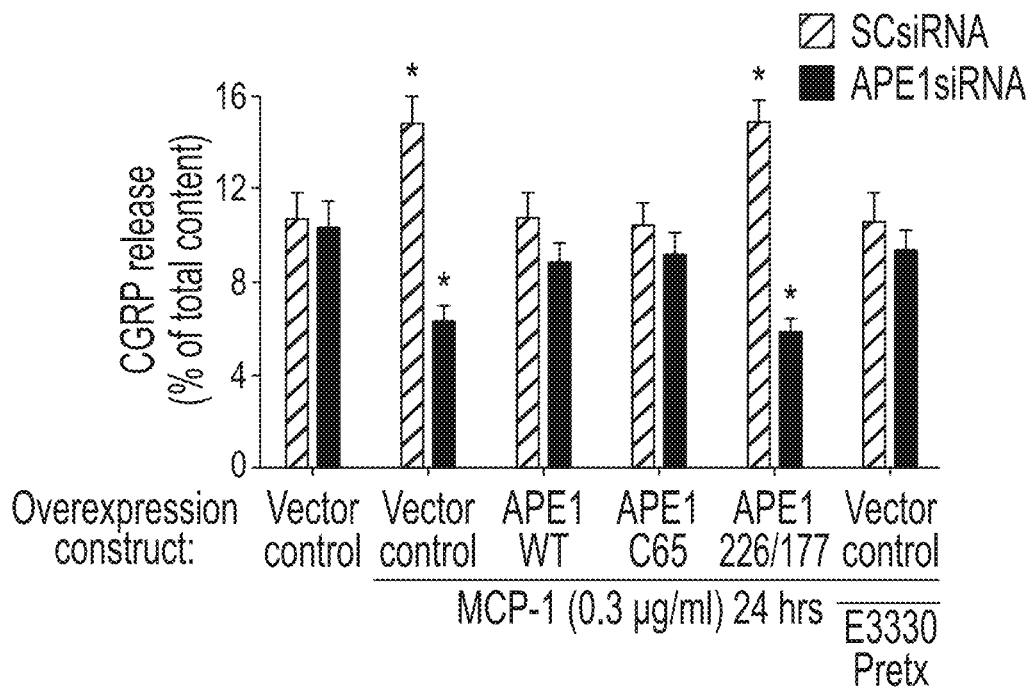

Using the same methods that were used in FIGS. 5A-5D, APE1 expression and activity was manipulated and then cultures were treated with MCP-1 (0.3 µg/ml) for the 24 hours immediately prior to experiments (FIG. 6A). As demonstrated in FIGS. 2A & 2B, SCsiRNA-treated sensory neurons exposed to MCP-1 had enhanced expression of pH2A.X (FIGS. 6B and 6C). Increasing the exogenous expression of wildtype or repair-competent APE1 prevented the ability of MCP-1 to increase pH2A.X; levels of pH2A.X were decreased to 36.9 and 33.6% of the MCP-1-induced increase in the presence of wildtype and C65 APE1, respectively. In contrast, exogenous expression of the repair-deficient APE1 did not prevent the MCP-1-induced expression of pH2A.X. Similar effects were observed in cultures treated with APE1siRNA; MCP-1 induced pH2A.X and this trended to be more extensive compared to the SCsiRNA-treated cultures. As observed with LPS, treatment of sensory neurons exposed to SCsiRNA or APE1siRNA with E3330 prevented the induction of pH2A.X by MCP-1. To determine whether these changes in pH2A.X expression correlated with changes in neuronal sensitivity, the release of CGRP stimulated by capsaicin (FIG. 6D) was examined. Following treatment with SCsiRNA, MCP-1 (0.3 µg/ml) enhanced the release of CGRP. This enhancement was not observed when APE1 expression was enhanced exogenously with either the wildtype APE1 or a repair-competent APE1 (C65 APE1). Exogenous expression of the repair-deficient APE1 (226/177); however, did not prevent the MCP-1 induced sensitization of CGRP release (FIG. 6D, light gray columns). In cultures treated with APE1siRNA, MCP-1 treatment caused a decrease in CGRP release, suggesting that the response to MCP-1 is shifted leftwards, based on the concentration response curve presented in FIG. 3, in cultures with reduced DNA repair activity. This decrease was reversed by exogenous expression of wildtype or repair-competent APE1, but unaffected by expression of repair-deficient APE1 (FIG. 6D, dark gray columns). As observed with the induction of pH2A.X expression, treatment of cultures with E3330 prevented the change in CGRP release induced by MCP-1 exposure (FIG. 6D). Collectively, these data support the notion that LPS induces double-strand DNA breaks in neuronal nuclei and that this DNA damage mediates changes in neuronal sensitivity.

Discussion

In this Example, it was investigated whether exposure of neuronal cultures to inflammatory mediators elicits DNA damage and a change in the sensitivity of sensory neurons. It was next sought to determine whether DNA damage and changes in neuronal sensitivity were reversed by enhancing the DNA base excision repair (BER) pathway. The results demonstrate that peripheral inflammation enhances DNA damage within the soma of sensory neurons innervating the inflamed tissue, as indicated by an increase in pH2A.X expression. An increase in pH2A.X expression is also apparent in sensory neuronal cultures, following exposure to LPS or MCP-1. In addition to DNA damage, exposure of sensory neuronal cultures to LPS or MCP-1 results in changes in the sensitivity of the neurons, as indicated by the stimulated release of the neuropeptide, CGRP, without altering resting release or the total content of CGRP. Genetic manipulation of APE1 expression or treatment with a small-molecule modulator of APE1 activity to enhance DNA repair via the base excision repair pathway attenuates DNA damage elicited by LPS or MCP-1. In addition to repairing the DNA damage, enhancing the DNA repair activity of APE1 reverses the inflammatory mediator-induced changes in neuronal sensitivity. Of interest, it was also demonstrated that DNA damage and changes in neuronal sensitivity induced by LPS are inhibited by the CCR2 antagonist, suggesting that long-term sensitization induced by TLR4 activation might be mediated through an increase in the production and putative autocrine activity of CCL2/MCP-1.

The signaling pathways by which inflammation alters the sensitivity of primary afferent neurons have been investigated extensively and include posttranslational modifications to reversibly alter the function of receptors, ion channels, or associated regulatory proteins and transcriptional regulation to alter the expression of receptors, ion channels, or neurotransmitters or to induce novel expression of these proteins to modulate the phenotype of sensory neurons (Neumann et al., 1996). To identify a causative role for DNA damage in maintaining neuronal sensitization induced by inflammation, neuronal cultures derived from DRG were utilized. The cultures were treated with the TLR4 or CCR2 ligands, LPS or MCP-1/CCL2, respectively, to mimic the effects of inflammation on neurons in culture. LPS is expressed on the outer membrane of gram negative bacteria, including the inactivated *Mycobacterium tuberculosis* present in complete Freund's adjuvant used in the in vivo inflammation studies and is an exogenous ligand for the TLR4 receptor. LPS enhances the expression of TNFα, IL-1β, COX-2 and MCP-1 in sensory neurons (Tse et al., 2014, Miller et al., 2015), thus recapitulating the activation of multiple pathways elicited by inflammation. In addition, LPS acutely enhances the sensitivity of sensory neurons as demonstrated by nociceptive behaviors following injection into the hindpaw of rodents (Ferreira et al., 1993, Calil et al., 2014) and by in vitro experiments, where LPS enhances the excitability and exocytotic activity of sensory neurons (Hou and Wang, 2001, Diogenes et al., 2011, Meseguer et al., 2014). MCP-1 is a cytokine that is upregulated in DRG by inflammation (Jeon et al., 2008), and released from DRG or dorsal spinal cord via stimulation of sensory neurons (Dansereau et al., 2008). MCP-1 exposure has been shown to upregulate the neuronal expression of TRPV1 and NaV1.8 (Kao et al., 2012), potentially mediated by the activation of NFκB (Tse et al., 2014, Zhao et al., 2014). MCP-1 also enhances the sensitivity of sensory neurons via posttranslational modifications, as evidenced by an increase in nociceptive behaviors following hindpaw injection (Dansereau et al., 2008) and by a direct stimulation of CGRP from cultures derived from neonatal DRG (Qin et al., 2005). MCP-1 is a ligand for the CCR2 receptor. Although the CCR2 is not expressed in DRG neurons derived from naïve animals, the CCR2 is expressed in DRG following inflammation or nerve injury (White et al., 2005, Miller et al., 2012, Zhang et al., 2013). Furthermore, the CCR2 is functionally active in cultures derived from DRG (Qin et al., 2005, Kao et al., 2012).

In addition to the activation of kinases and transcription factors to elicit hypersensitivity, inflammation also enhances the generation of reactive oxygen and nitrogen species, which play a role in mediating changes in neuronal sensitivity. Inflammatory mediators enhance the production of ROS/RNS via enzymatic (NADPH oxidase) and autooxidation reactions (via metabolism-induced increases in electron transport chain leakage) (Bauerova and Bezek, 1999, Babior, 2000, Remans et al., 2005, Ibi et al., 2008). ROS/RNS function as agonists for the TRPV1 and TRPA1 channels (Andersson et al., 2008, Sawada et al., 2008, Keeble et al., 2009, Ito et al., 2013, Lin et al., 2015). In addition to the acute effects of ROS to enhance TRPV1 and TRPA1 sensitivity, an intracellular increase in free radical moieties can lead to the oxidation of molecules, including nucleic acids, proteins, and lipids, leading to potentially serious consequences for sensory neurons. It was recently demonstrated that DNA damage was a causative factor in altering the sensitivity of neurons following treatment with cisplatin (REF). The studies identified that changes in neuronal sensitivity could be reversed by repair of oxidative lesions induced by cisplatin, suggesting an important role for ROS/RNS in modulating neuronal sensitivity by damaging DNA. These findings led to the hypothesis to that inflammation-induced production of ROS/RNS and subsequent oxidative DNA damage is critical for the maintenance of changes in neuronal sensitivity induced by inflammation.

Because ROS/RNS can be produced by endogenous metabolic activity, oxidative stress secondary to injury (Kruman and Schwartz, 2008), environmental toxins, (Kisby et al., 1999) and drugs (Ahles and Saykin, 2007) and because ROS/RNS elicits oxidative DNA damage, sensory neurons have endogenous antioxidant mechanisms to combat excessive production of ROS/RNS. In the event that the free radical moieties overwhelm the endogenous antioxidants, sensory neurons also have DNA repair mechanisms to repair oxidative DNA damage. Although sensory neurons are postmitotic, DNA damage can still have critical consequences on the integrity of gene transcription and for the maintenance of neuronal homeostasis (Fishel et al., 2007b), therefore sensory neurons repair DNA damage through the XX pathways (REFS). Of these various DNA repair pathways in neurons, the base excision repair pathway (BER) is predominant (Fishel et al., 2007b) and is responsible for the repair of DNA caused by oxidative damage. BER involves several steps to repair a DNA lesion, including removal of the oxidatively damaged base by a DNA glycosylase to create an apurinic/apyrimidinic site (AP-site), cleavage of the DNA backbone by apurinic/apyrimidinic endonuclease 1/redox factor (APE1/Ref-1 or APE1) to produce a 3'-OH terminus in preparation for a DNA polymerase and ligase to insert a new base and ligate the DNA backbone, respectively. Failure to repair oxidative DNA damage can result in mutations, obstruction of DNA replication, and genetic instability. As mentioned before, the importance of the BER pathway, specifically the activity of APE1, in protecting isolated sensory neurons from the toxic effects of anticancer treatment has been examined. Reducing the expression of APE1 increases the neurotoxicity produced by cisplatin exposure, whereas, augmenting the activity of APE1 lessened the neurotoxicity (Vasko et al., 2005, Jiang et al., 2008b, Jiang et al., 2009, Kelley et al., 2014). In addition to the AP endonuclease function of APE1, the enzyme also has activity to modulate the redox status of transcription factors to regulate their function (REF). The findings that overexpression of the DNA repair-competent APE1, but not the redox-competent APE1, suggest that the DNA repair component of APE1 is essential to reverse sensitization induced by inflammatory mediators. The implication, therefore, is that exposure of sensory neurons to inflammation can elicit hypersensitivity through a variety of signaling pathways; however, the maintenance of this sensitization is dependent on DNA damage.

It is not known how exposure of sensory neurons to MCP-1 elicits the generation of DNA damage. Because MCP-1 generates DNA damage that can be reversed by enhancing BER, it is hypothesized that the DNA damage induced by MCP-1 was mediated by an increase in ROS/RNS. Reactive oxygen and nitrogen species can be generated by multiple sources: a major driver of ROS/RNS generation is respiratory chain activity in the mitochondria, yet non-mitochondrial ROS/RNS can be produced by enzymes such as NADPH oxidase, xanthine oxidase, cyclooxygenase, cytochrome p450, and lipoxygenase (Sauer et al., 2001, Holmstrom and Finkel, 2014). Because it was found that the effects of LPS could be attenuated by a CCR2 antagonist, it is believed that the maintenance of hypersensitivity induced by LPS is mediated through activation of TLR4 and subsequent upregulation of MCP-1/CCL2. This finding was surprising because activation of TLR4 elicits the generation of ROS/RNS in macrophages (Zhang et al., 2015), yet in neurons TLR4 activation cannot maintain sensitivity without activation of the CCR2. Therefore, it is believed that the quantitative, spatial and temporal aspects of ROS/RNS generation are critical for inducing DNA damage and will be studied further.

What is still unclear is how seemingly random oxidative DNA damage elicited by inflammation or inflammatory mediators can elicit such a reproducible phenotype to sustain neuronal hypersensitivity. The major oxidative DNA lesion formed by oxidative stress, 8 oxoG, has been suspected to contribute to the development of inflammation and aging (Shigenaga et al., 1994, David et al., 2007); however, recent data suggests that the removal of 8oxyG by 8-oxoguanine-DNA glycosylase-1 (OGG1) promotes the formation of an OGG1-8oxoG complex that has guanine nucleotide exchange factor properties and is the causative trigger for disruption of cellular homeostasis rather than the total 8oxoG burden (Aguilera-Aguirre et al., 2014). These data seemingly contradict the findings, as promotion of BER decreases the alterations in sensitivity induced by DNA damage. Further experiments examining the role of OGG1 in neuronal function are ongoing to discern how 8oxoG affects sensory neurons. The redox function of APE1 already has been recognized as contributing to an inflammatory response in other cell types (Jedinak et al., 2011), but the present disclosure is the first to implicate a protective role for the DNA repair function of APE1. It is believed that posttranslational and transcriptional effects of inflammatory mediators can mediate the induction of hypersensitivity in neurons, but DNA damage maintains these changes due to the impact of oxidative DNA lesions on transcriptional activity. Thus, inflammation could contribute to functional changes in neurons that are reproducible and that enhanced DNA repair could reverse the functional changes in neurons induced by the damage. Oxidative damage to DNA is known to alter the ability of transcription factors to recognize and bind promoter regions (Ziel et al., 2004, Gillespie et al., 2009, Pastukh et al., 2015), thus the DNA damage induced by inflammation might be reproducible because of damage to promoter/repressor regions of genes or transcription factors that are already activated by inflammation (Ruchko et al., 2009).

In conclusion, the present disclosure demonstrates that inflammation or exposure to inflammatory mediators elicits DNA damage in sensory neurons. By enhancing base excision repair, it is demonstrated that this DNA damage mediates the maintenance of neuronal hypersensitivity induced by inflammatory mediators.

EXAMPLE 2

In this Example, APX3330 was analyzed for its effects on DNA repair activity.

Neuroblastoma cells were implanted subcutaneously into the right flanks of 6-wk old male NSG mice and allowed to proliferate until tumor volumes ≥150 mm$^3$. Mice were then randomized for treatment with cisplatin±APX3330 treatment. Cisplatin and APX3330 were administered concurrently for 3 weeks (Day 0-Day 17) and endpoints of neuronal toxicity were assessed within the DRG of mice at several time points following the last dose of cisplatin.

When isolated sensory neurons were exposed to APX3330, a concentration-dependent increase in Ref-1/APE1 endonuclease activity occurred, which is not observed in tumor cells. Although APX3330 is a targeted inhibitor of Ref-1/APE 1's redox function, it appears that, in the setting of sensory neurons, it can also enhance the protein's DNA repair (AP endonuclease) activity (FIGS. 7A-7E). APX3330 causes the protein to unfold over time. This unfolding primarily alters the amino end of Ref-1/APE1, affecting its interactions with downstream transcription factor targets by perturbing the equilibrium of the protein's folded/unfolded states and facilitating repair activity. This disengagement of Ref-1/APE1 from its Ref-1/APE1 redox activity could enhance Ref-1/APE1 repair endonuclease activity.

Figure 7A:
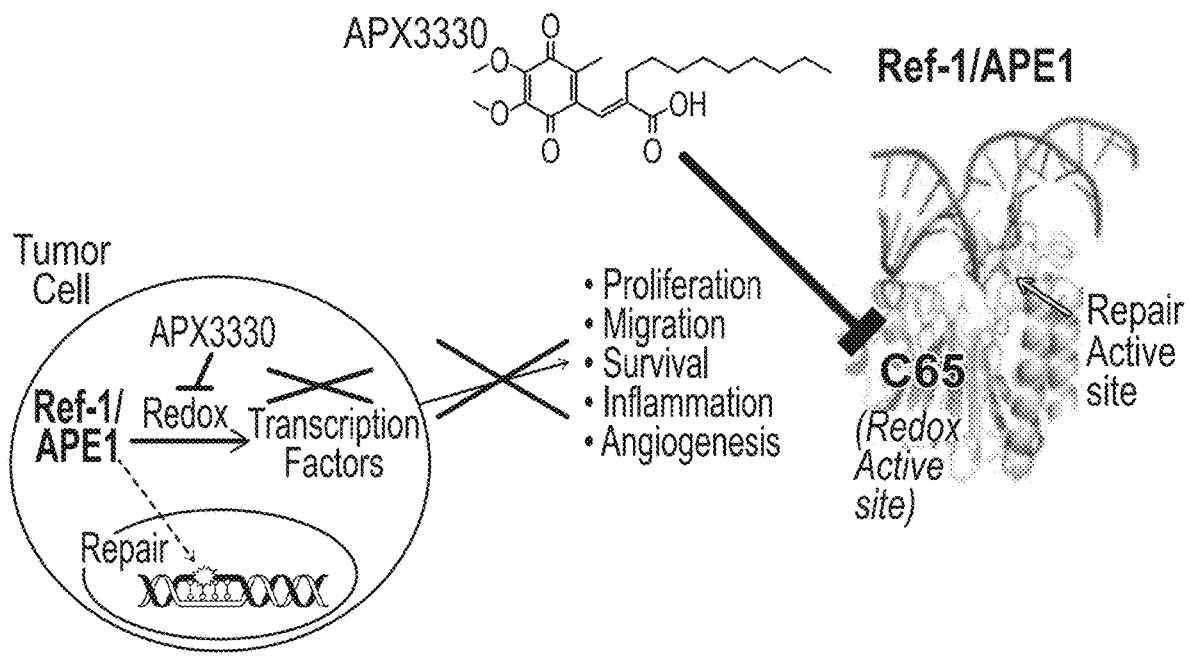
FIGS. 7A-7E depict the differential role of Ref-1/APE1 redox inhibition in sensory neurons vs. tumor cells.
Figure 7B:
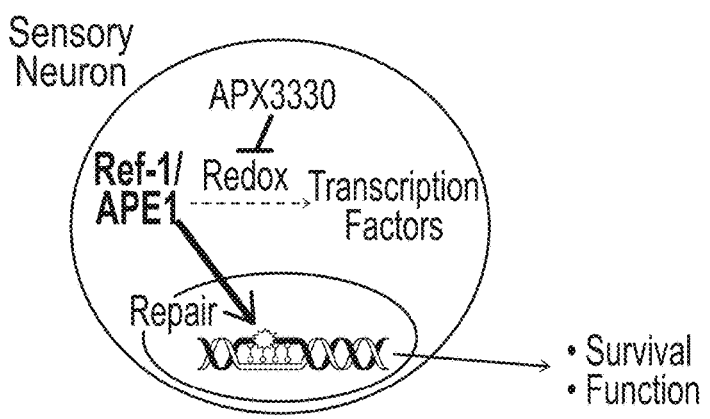
Figure 7C:
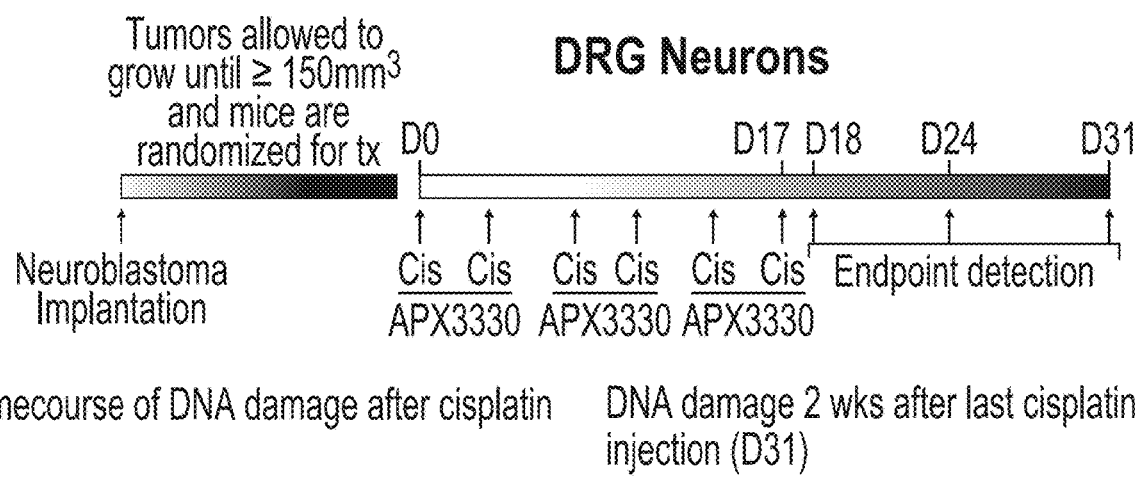
Figure 7D:
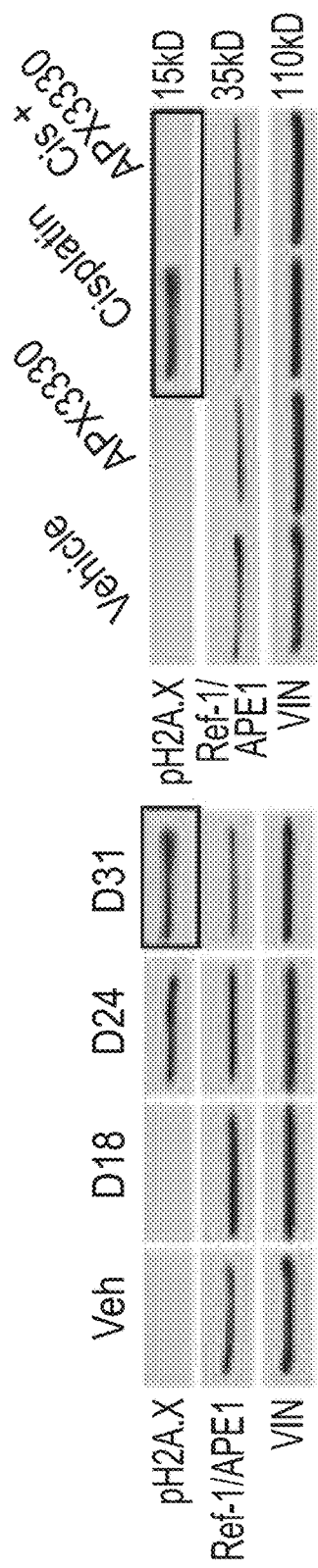
Figure 7E:

A critical property of any putative therapeutic for neurotoxicity is that it will not compromise the anticancer function of the treatment(s) administered. Importantly, the enhancement of DNA repair activity by APX3330 was not observed in mitotic cells. It has been previously shown that APX3330 negatively affects the growth and/or survival of tumor cell lines, patient-derived cell lines, and tumors in animal models. Therefore, it is possible that APX3330 could protect postmitotic cells without altering the effects of anticancer drugs on tumor cells (FIGS. 7C-7E). Additionally, APX3330 did not affect cisplatin or oxaliplatin's tumor-killing efficacy in vivo, yet it protects DRG neurons from oxidative DNA damage (data not shown). In healthy cells, it appears that the DNA repair function—not the redox function of Ref-1/APE1—is necessary for sensory neuronal survival/function. That is opposite from tumor cells. Collectively, these data support the notion that APX3330 can be neuroprotective against cancer therapy without compromising treatment.

EXAMPLE 3

In this Example, APX3330 analogs were analyzed for their ability to protect against neurotoxicity-induced by cisplatin or oxaliplatin while not diminishing the anti-tumor effect of the platinum. Also, the analog APX2009 was assessed for its anti-tumor effects in neuroblastoma cell lines as well as in a 3D spheroid pancreatic tumor model.

Materials and Methods

Materials

General tissue culture supplies were obtained from Invitrogen (Carlsbad, Calif.), and chemicals were purchased from Sigma-Aldrich (St. Louis, Mo.). For sensory neuronal cultures, poly-D-lysine and laminin were purchased from Sigma-Aldrich (St. Louis, Mo.), nerve growth factor from Harlan Bioproducts for Science (Indianapolis, Ind.), and normocin from Invivogen (San Diego, Calif.). Mouse monoclonal antihuman APE1 antibodies were raised in the laboratory and are available from Novus Biologicals (Littleton, Colo.). Mouse monoclonal anti-phospho-H2AX antibodies were from EMD Millipore (Billerica, Mass.) and (3-Actin monoclonal antibody from Thermo Fisher Scientific (Fremont, Calif.). Chemiluminescence secondary antibodies were from Roche Diagnostics Corp. (Indianapolis, Ind.).

Cisplatin was purchased from Sigma-Aldrich Inc. (St. Louis, Mo.), and oxaliplatin was purchased from LKT Laboratories, Inc. Cisplatin was initially dissolved in N,N-dimethylformamide (Sigma-Aldrich) and stored as a 40 mM solution at −80° C. and oxaliplatin dissolved in PBS and stored as a 5 mM stock at −80° C. Before drug treatment, the stocks were diluted in F-12 growth medium and added to cultures and exposed for 24-72 hours. The Animal Care and Use Committee at Indiana University School of Medicine, Indianapolis, Ind. approved all procedures used in these studies.

Synthesis of New Chemical Entities

Complete details of synthesis of the new, second-generation analog compounds of APX3330 is provided in Sardar Pasha Sheik Pran Babu et al., Ref-1/APE1 inhibition with novel small molecules blocks ocular neovascularization, available online Apr. 6, 2018; doi: 10.1101/296590, which is incorporated by reference to the extent it is consistent herewith. The compounds were synthesized by Cascade Custom Chemistry, Eugene, Oreg. 97401 USA. In summary, iodolawsone, 2-iodo-3-hydroxy-1,4 naphthoquinone a common intermediate, is available from Cascade Custom Chemistry. As described, iodolawsone in a subsequent reaction is treated with methacrylic acid or 2-propylacrylic acid, with oxalyl chloride and the corresponding amine, and with sodium methoxide in methanol to yield (2E)-2-[(3-methoxy-1,4-dioxo-1,4-dihydronaphthalen-2-yl)methylidene]-N,N-dimethylpentanamide (APX2007), (2E)-2-[(3-methoxy-1,4-dioxo-1,4-dihydronaphthalen-2-yl)methylidene]-N,N-diethylpentanamide (APX2009), and (2E)-2-(3-methoxy-1,4-dioxo-1,4-dihydronaphthalen-2-yl)-N,N,2-trimethylprop-2-enamide (APX2032). Further information can be found in the issued patent "Quinone Compounds for Treating Ape1 Mediated Diseases" (Mark R. Kelley and James H. Wikel), U.S. Pat. No. 9,193,700, issued on 11.24.15, which is hereby incorporated by reference to the extent it is consistent herewith.

Chemical Structure Presentation

Marvin was used for drawing, displaying and characterizing chemical structures, substructures and reactions, Marvin 15.8.24.0, 2015, ChemAxon (http://www.chemaxon.com). Calculator Plugins were used for structure property prediction, Marvin 15.8.24.0, 2015, ChemAxon (www.chemaxon.com). Molecular modeling was performed using the Open Eye Scientific software OMEGA (OMEGA 2.5.1.4) (Hawkins et al., 2010) and ROCS (ROCS 3.2.1.4: OpenEye Scientific Software, Santa Fe, N Mex. www.eyesopen.com) (Hawkins et al., 2007). Molecular visualization was performed using the Open Eye Scientific software VIDA (OpenEye Scientific Software, Santa Fe, N. Mex. www.eyesopen.com).

Sensory Neuronal Cultures

Primary cultures of sensory neurons were harvested and maintained as previously described (Vasko et al., 2005). Briefly, adult male Sprague-Dawley rats (150-175 g; Harlan, Indianapolis, Ind.) were euthanized by $CO_2$ asphyxiation and dorsal root ganglia (DRG) dissected from all spinal levels, transferred to into a collagenase solution (1 mg/ml), incubated for 1 hour at 37° C., then dissociated by mechanical agitation. Approximately 30,000 cells or 60,000 cells were plated into each well of 12-well or 6-well culture plates, respectively. All culture dishes were precoated with poly-D-lysine and laminin. Cells were maintained in F-12 media supplemented with 10% horse serum, 2 mM glutamine, 100 µg/ml Normocin™, 50 µg/ml penicillin, 50 µg/ml streptomycin, 50 µM 5-fluoro-2'-deoxyuridine (Invitrogen), 150 µM uridine, and 30 ng/ml of NGF in 3% CO2 at 37° C. Growth medium was changed every other day. Experiments were performed after cells were maintained in culture for 12-14 days.

Neuronal Cell Viability

Sensory neuronal culture trypan blue exclusion analysis was performed as previously described (Vasko et al., 2011). Cells were detached by adding a 0.05% trypsin-EDTA solution and media to each well. An equal volume of 0.4% (w/v) trypan blue in PBS was added to the cell suspension and the numbers of living cells (i.e., those that exclude the dye) were counted under a phase contrast microscope using a hemacytometer. Percent survival was calculated as the percent of live cells divided by the total cell number (including dead and live cells).

Cell Line Authentication and Characterization

The IMR32 and SK—N—SH cell lines were obtained from the American Type Culture Collection and grown in RPMI-1640 supplemented with 10% FBS. Cell line identity was confirmed by DNA finger print analysis (IDEXX BioResearch) for species and base-line short-tandem repeat analysis testing. All cell lines were 100% human and a 9-marker short-tandem repeat analysis is on file.

Cell Proliferation Assay

Cells were seeded in 96-well plates (IMR32: 1000 cells/well; SK—N—SH: 3000 cells/well) and treated for 5 days with APX2007, APX2009, APX2032, or APX3330 (also referred to herein as "E3330"). Final DMSO concentration was <0.1%. Cell viability was determined using the methylene blue assay as previously described (Tonsing-Carter et al., 2015). Each experiment was performed in triplicate and repeated three times. The percent viabilities, normalized to the control, were graphed and $ED_{50}$ values determined using the Chou-Talalay method (Chou and Talalay, 1984).

Immunoblotting

Immunoblotting was performed as previously described (Kelley et al., 2014). Briefly, cells were lysed in RIPA buffer (Santa Cruz Biotechnology; Santa Cruz, Calif., USA) and protein was quantified using the Lowey assay. Proteins were separated by electrophoresis on a 4-12% SDS-polyacrylamide gel. The gel was transferred to a PVDF membrane and incubated overnight at 4° C. in Tris-buffered saline containing 0.1% Tween-20 (TBST) and 5% nonfat dry milk while gently agitating. Mouse monoclonal antihuman Ape1 antibodies (1:500), mouse monoclonal anti-phospho H2AX antibodies (1:1000), or (3-Actin monoclonal antibody (1:1000) were added to the blocking solution and incubated overnight at room temperature while gently agitating. Antibody binding was detected following appropriate secondary antibody methods using chemiluminescence. The density of the bands was measured using QUALITYONE® software from Bio-Rad (Hercules, Calif.) and data expressed as density normalized to actin.

Measurement of Calcitonin-Gene Related Peptide Release

For release experiments, cell cultures were washed with HEPES buffer consisting of (in mM) 25 HEPES, 135 NaCl, 3.5 KCl, 2.5 $CaCl_2$, 1 $MgCl_2$, 3.3 D-glucose, and 0.1% bovine serum albumin, pH 7.4 and maintained at 37° C. They then were incubated for successive 10-minute intervals with 0.4 ml of HEPES buffer alone (basal release), with buffer containing 30 nM capsaicin, then with buffer alone (to assess return to basal release). After each incubation, the buffer was removed and the amount of immunoreactive calcitonin-gene related peptide (CGRP) in each sample was measured using radioimmunoassay (RIA) as previously described (Chen et al., 1996). At the end of the release protocol, CGRP is extracted from the cultures and total content measured using RIA. Since treatments did not significantly alter total content, release data are presented as fmol of peptide released/well/10 min.

AP Endonuclease DNA Repair Assay

Inhibition or enhancement of APE1 DNA repair endonuclease activity was performed as previously described (Bapat et al., 2010). The APE1 repair activity assay was performed in a plate assay using two annealed oligonucleotides (5'-6-FAM-GCCCCC*GGGGACGTACGATATCCCGCTCC-3' (SEQ ID NO:3) and 3'-Q-CGGGGGCCCCCTGCATGC-TATAGGGCGAGG-5' (SEQ ID NO:4)) containing a quencher on one strand and a fluorescent 6-FAM label with tetrahydrofuran as an AP site mimic. Oligo cleavage at the AP mimic site results in 6-FAM release and detection. The fluorescence was read at five, one-minute intervals using a Tecan Ultra plate reader (Chemical Genomics Core, Indiana University School of Medicine). The rate of the reaction was used to determine the change in APE1 repair activity as compared to the vehicle control.

Electrophoretic Mobility Shift Assay (EMSA)

EMSAs were performed as described (Luo et al., 2012). Purified APE1 was reduced with 1.0 mM DTT for 10 minutes and diluted to a final concentration of 0.006 mM with 0.02 mM DTT in PBS. Reduced APE1 was added to EMSA reaction buffer (10 mM Tris (pH 7.5), 50 mM NaCl, 1 mM $MgCl_2$, 1 mM EDTA, 5% [vol/vol] glycerol) with 2 mL 0.007 mM protein mixture (1:1) of purified truncated c-Jun and c-Fos proteins containing DNA-binding domain and leucine zipper and incubated for 30 minutes at room temperature. The EMSA assay was performed as previously described (Luo et al., 2008; Nyland et al., 2010; Kelley et al., 2011; Luo et al., 2012).

Transient Luciferase Reporter Assays

Reporter assays were performed as previously described (Georgiadis et al., 2008; Kelley et al., 2011; Cardoso et al., 2012b; Luo et al., 2012). Cells were transfected with NF-κB-Luciferase construct containing an NF-κB-response promoter and driving the expression of a luciferase gene and a Renilla luciferase control reporter vector pRL-CMV. After a 24-hour transfection period, cells were lysed, and Firefly and Renilla luciferase activities were assayed using Renilla luciferase activity for normalization. All of the transfection experiments were performed in triplicate and repeated at least three times in independent experiments. Data are expressed as mean±standard error from a representative experiment, and Student's t tests were performed.

Tumor and Cancer Associated Fibroblast (CAF) 3D Co-Cultures

Patient-derived tumor cells and CAF19 cells were a kind gift from Dr. Anirban Maitra (The Johns Hopkins University M.D. Anderson Cancer Center) (Jones et al., 2008). All cell lines were authenticated via STR analysis (IDEXX BioResearch) and checked routinely for mycoplasma contamination. Ultra low attachment 96-well plates (Corning Inc., Life Sciences) were used to generate 3-dimensional tumor spheroids in the presence and absence of CAFs, as described previously (Sempere et al., 2011; Arpin, 2015). TdTomato-labeled PDAC cells and EGFP-labeled CAFs are resuspended in colorless DMEM media containing 3% Reduced Growth Factor Matrigel (BD Biosciences) and 5% FBS at a cell ratio of 1:4 (tumor:CAF) and fed on days 4 and 8 following plating. Both cell populations are quantitated for intensity and area via Thermo ArrayScan at day 12 of co-culture.

Pharmacokinetics (PK) and P450 Metabolism Analysis

PK studies were performed in the IU Simon Cancer Center Clinical Pharmacology Analytical Core (CPAC), as previously described for E3330 (Fishel et al., 2011) and standards for the compounds used. P450 metabolism studies using human microsomes were also performed in CPAC directed by Dr. David Jones.

Statistical Analysis

Data is expressed as the mean±SEM from a minimum of three independent harvests or experiments. Statistically significant differences between controls and various treatments were assessed using Student t-tests. Differences in cell survival using trypan blue exclusion, gamma-H2AX (pH2AX), and CGRP release were determined using two-way analysis of variance (ANOVA) and Tukey's post hoc test.

Results

Figure 8A:
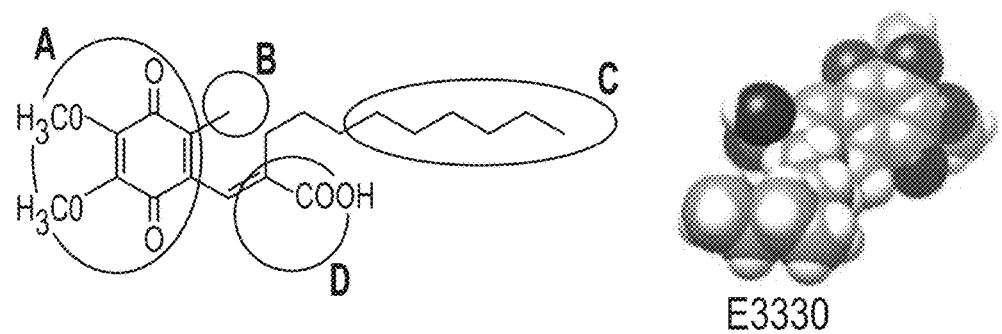
FIGS. 8A & 8B depict new chemical entities (NCE); E3330 analogs.
Figure 8B:
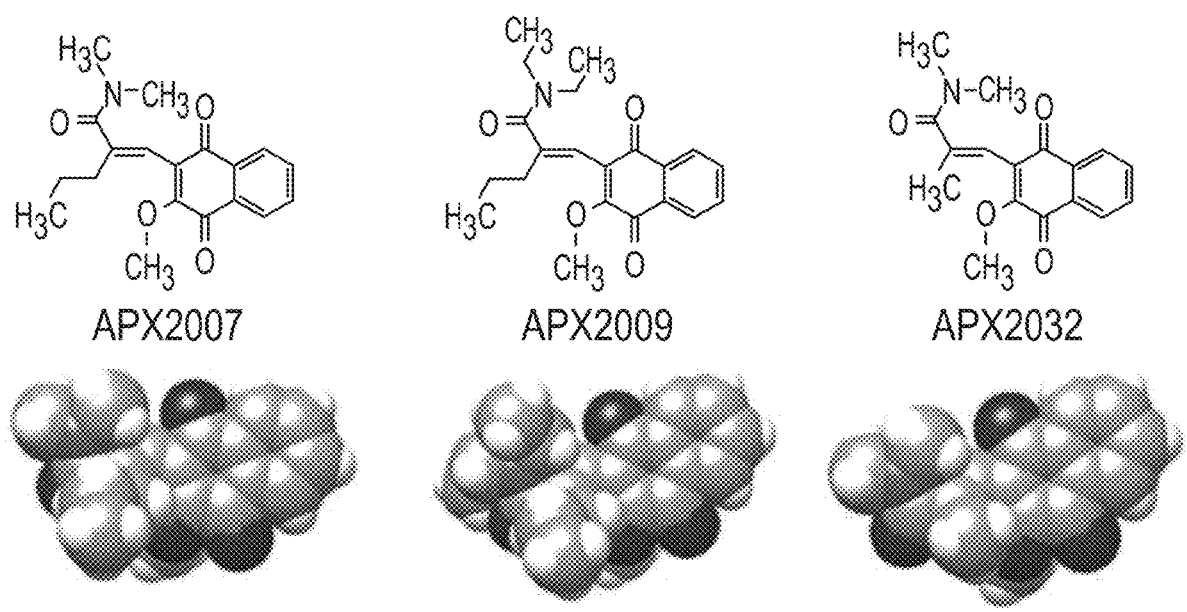
Figure 9A:
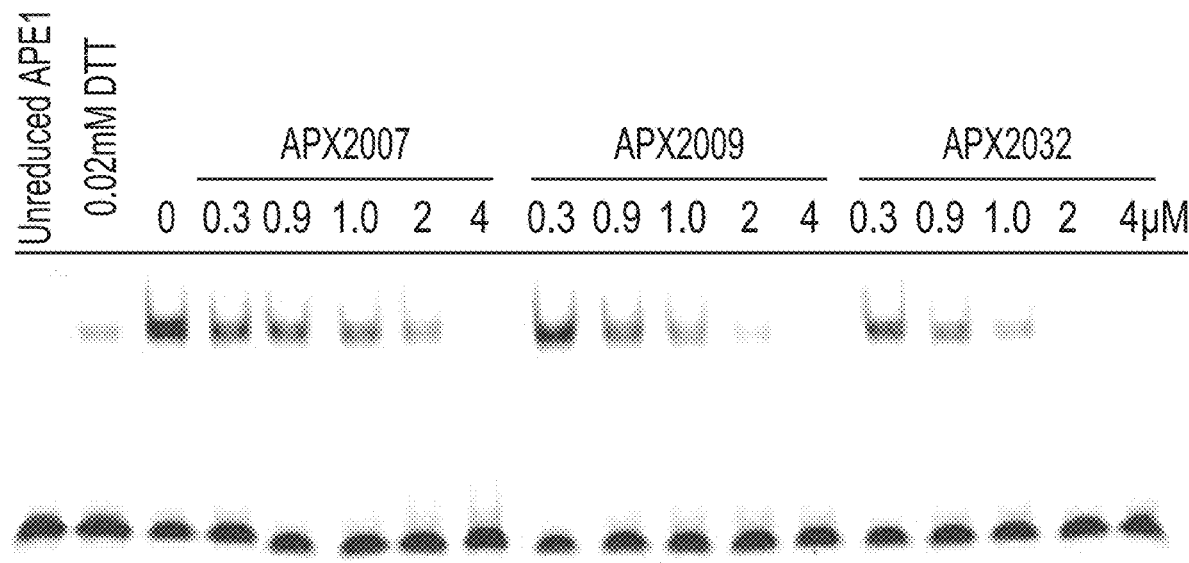
FIGS. 9A-9D depict the identification and characterization of chemical analogues to APX3330 (E3330) targeting APE1 for the prevention of chemotherapy-induced peripheral neuropathy (CIPN).

Chemical Synthesis of E3330 Analogs, Validation of Redox Inhibition and Pharmacokinetics A number of analogs of E3330 wre synthesized by replacing the core dimethoxybenzoquinone (A) with a napthoquinone ring, the methyl group (B) on the ring structure with various halogens or hydrogen, and shortening the carbon chain (C) on the double bond to modulate activity (FIG. 8A). In continuing efforts, the carboxylic acid moiety (D) was modified in concert with shortening the carbon chain (C) on the double bond. These changes modified two physical properties of the structure. E3330 exists as a charged molecule at physiological pH. Amide derivatives of the carboxylic acid (D), which are not a charged supporting chemical feature were prepared. In addition, E3330 has a very lipophilic carbon chain, which is believed to be a modifiable feature. The new structures have significantly shorter carbon chains (C) on the double bond and are therefore less lipophilic. Detailed synthesis data can be found in U.S. Pat. No. 9,089,605, which is hereby incorporated by reference to the extent it is consistent herewith. Three new structures from the compounds made (FIG. 8B) were analyzed in redox APE1 electrophoretic mobility shift assay (EMSA) studies to determine which compounds affect the redox function of APE1. The compounds had redox inhibition $IC_{50}$s of: APX2007 2 μM, APX2009 1 μM, and APX2032 1 uM (FIG. 9A). E3330 has been previously presented and has an $IC_{50}$ of 25 uM in similar assays.

Figure 9B:
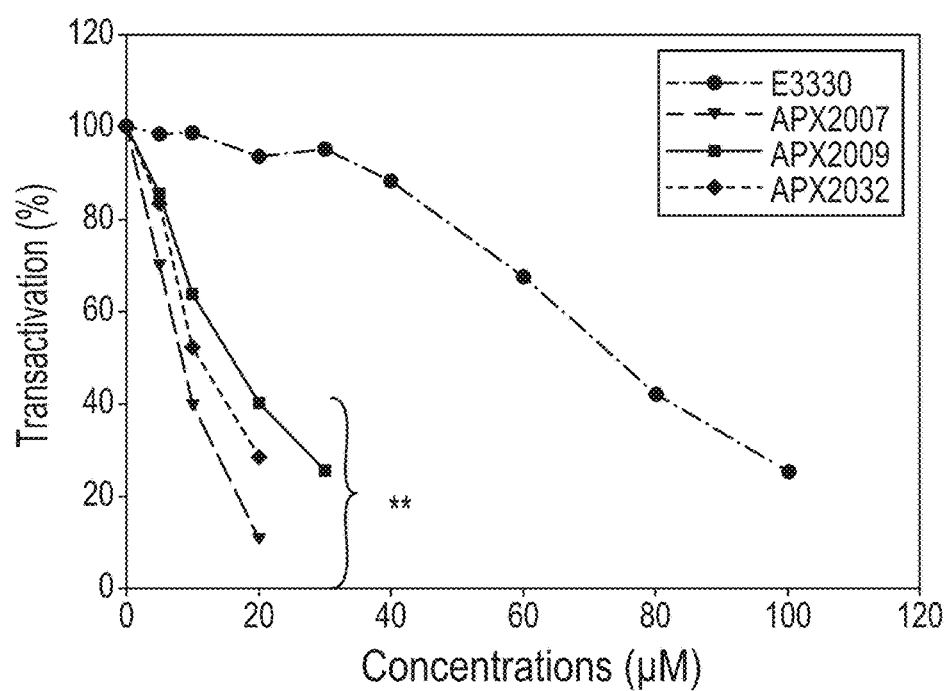
Figure 9C:
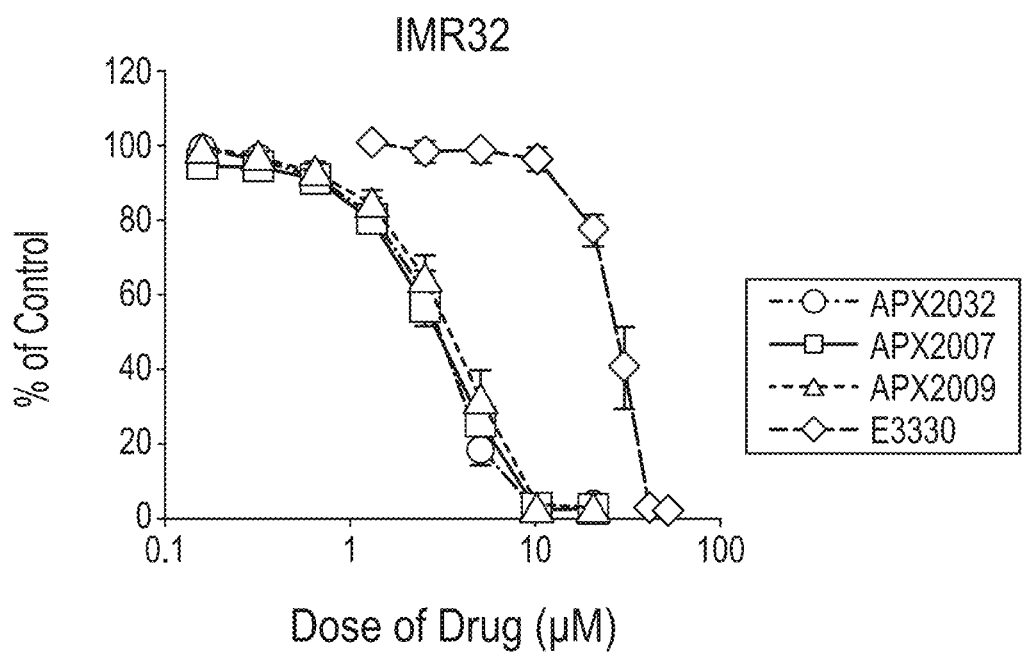
Figure 9D:
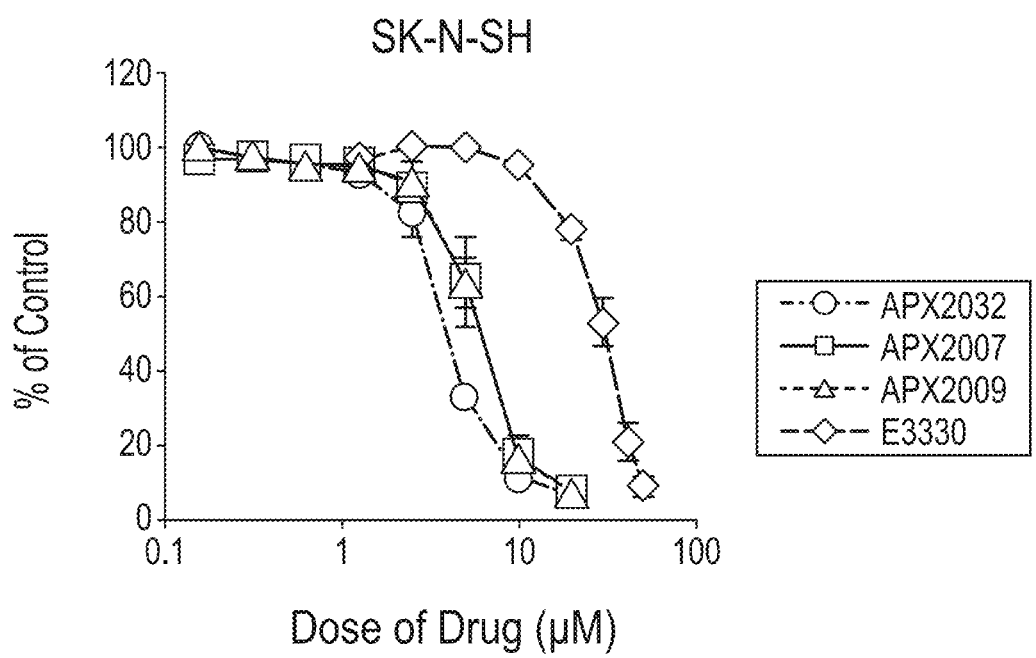

Reporter transactivation assays were performed to verify the new compounds as effective in cells and hitting their target APE1 which, in this assay, regulates NFκkB function. In these assays, all three compounds, APX2007, APX2009 and APX2032, demonstrated similar inhibition of NFκB binding to the reporter construct with an IC50 of 7 μM, while E3330 has an activity of 45 μM (FIG. 9B). Additionally, the $ED_{50}$ for tumor cell killing was determined in two neuroblastoma cell lines, IMR32 (p53 wt, MYCN amplified) and SK—N—SH (p53 wt, MYCN non-amplified) (FIGS. 9C & 9D). All three compounds had a reduced $ED_{50}$ compared to E3330; 7-10 fold greater in IMR32 cells and 4-6 fold greater in SK—N—SH cells (FIGS. 9C & 9D). The enhanced tumor cell killing data is consistent with the increased efficacy of the compounds on APE1 function as demonstrated by EMSA and transactivation data in FIG. 10. The pharmacokinetic profile of APX2009 was also assessed. As shown in FIGS. 11A & 11B, the half-life of APX2009 is 25.8 hours compared to 3.6 hours for E3330, or an approximate 7-fold half-life increase. Additionally, using human microsomes in a P450 metabolism analysis, APX2009 had a 173 vs 20-minute half-life or an 8.7-fold increase (FIGS. 11A & 11B).

Figure 12A:
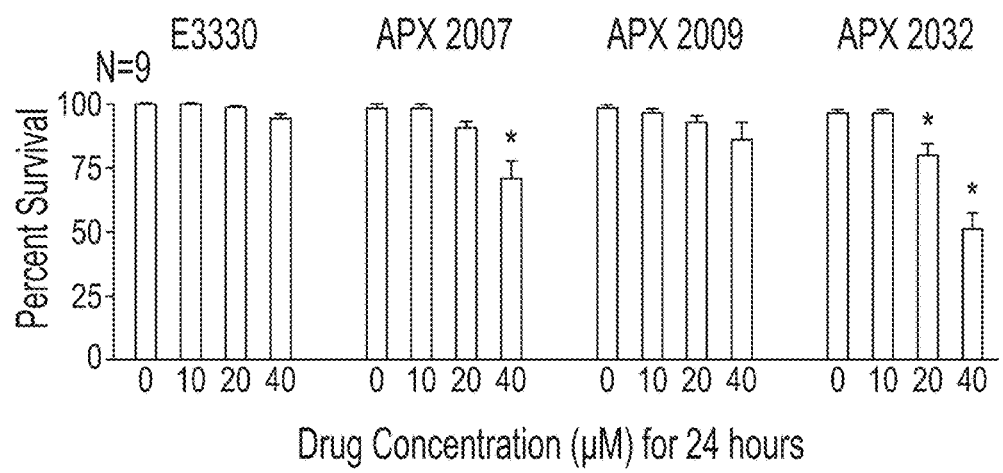
FIGS. 12A & 12B depict that pretreatment with E3330 and APX2009, but not APX2007 or APX2032, attenuated cisplatin-induced cell death in sensory neuronal cultures.

When the sensory neuronal cultures were exposed to E3330 at 10, 20 or 40 µM for 24 hours, there was no significant cell death as measured by trypan blue exclusion (FIG. 12A). In a similar manner, exposing cultures to various concentrations of APX2009 did not result in a significant reduction in cell viability (FIG. 12A). In contrast, treating cells with 40 µM APX2007 for 24 hours or with 20 µM or 40 µM APX2032 for 24 hours resulted in a significant reduction in cell viability (FIG. 12A). In a similar manner exposing cultures to 20 or 40 µM APX 2007, or APX2032 for 72 hours caused a significant increase in cell death (data not shown).

DNA repair activity assays were performed as previously described (Bapat et al., 2010). As shown in FIGS. 13A-13D, only APX2009 demonstrated a stimulation of APE1 repair activity in this assay and in the nanomolar range, a significant increase in activity compared to E3330 (FIGS. 11A & 11B). APX2007 and APX2032 had no effect, either for stimulation or inhibition of APE1 endonuclease activity.

Figure 12B:
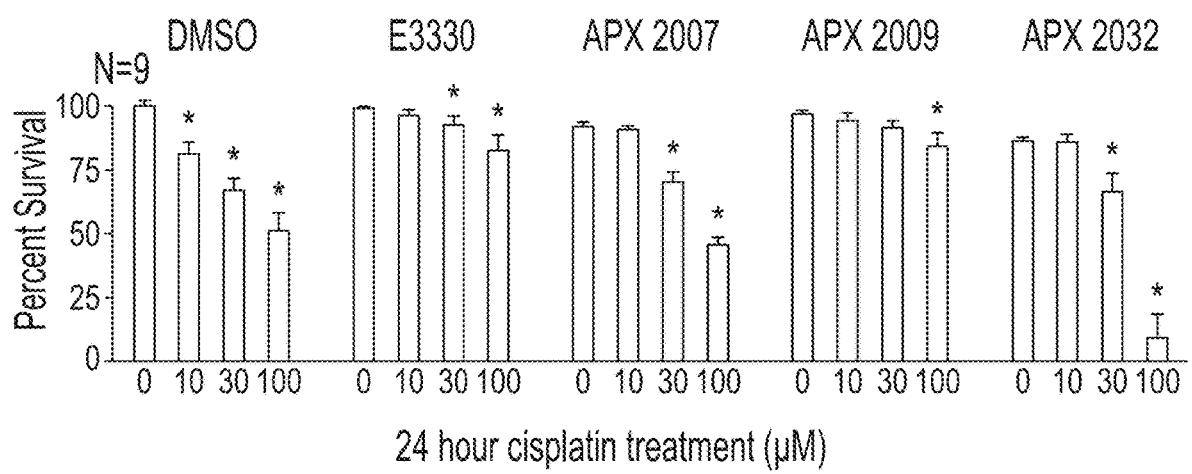
Figure 13A:
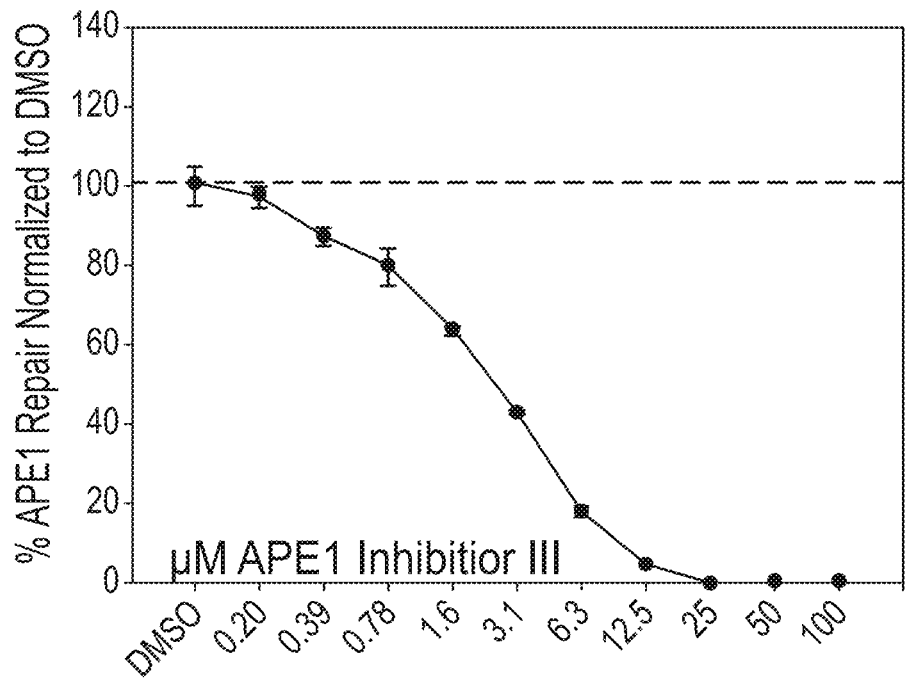
FIGS. 13A-13D depict results of DNA repair assays of APX3330 chemical analogues (Inhibitor III (FIG. 13A); APX2007 (FIG. 13B); APX2009 (FIG. 13C; APX 2032 (FIG. 13D)).
Figure 13B:
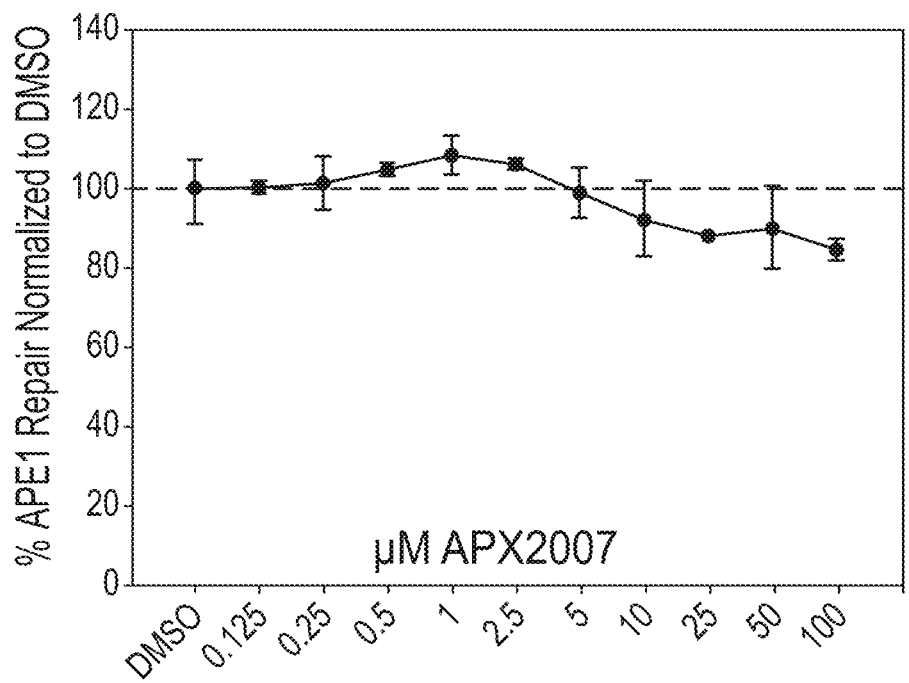
Figure 13C:
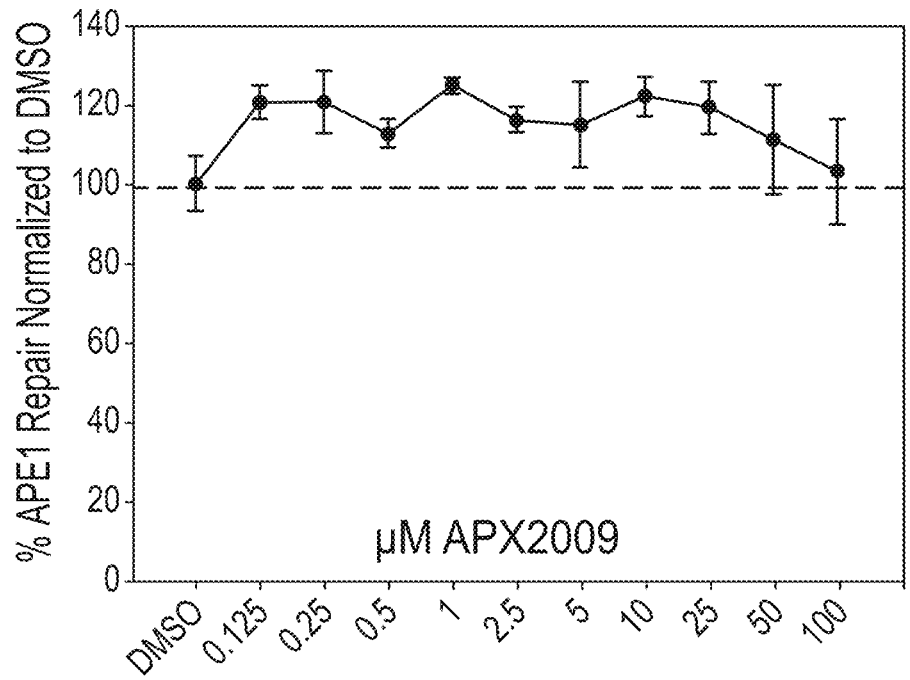
Figure 13D:
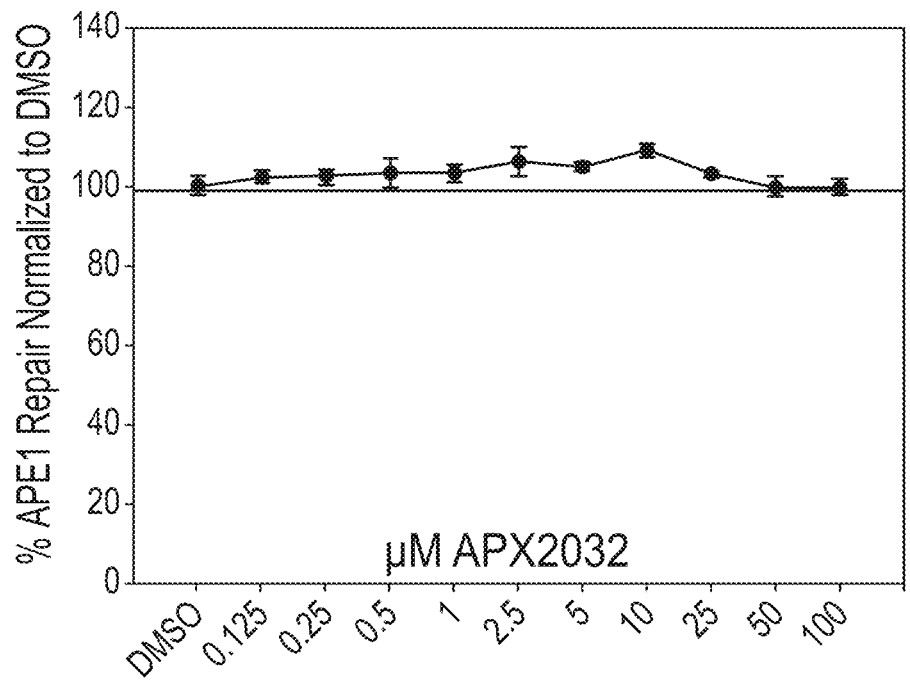

E3330 and APX2009, But Not APX2007 or APX2032, Attenuated Cisplatin-Induced Cell Death in Sensory Neuronal Cultures Since exposing neuronal cultures to E3330 is neuroprotective (Vasko et al., 2005; Jiang et al., 2008; Vasko et al., 2011; Kelley et al., 2014), whether E3330 and other analogs would affect cisplatin-induced cell death in cultures was assessed. Exposing neuronal cultures to increasing concentrations of cisplatin for 24 hours causes a concentration-dependent reduction in cell viability to 66±5% and 50±7% for 30 and 100 µM, respectively (FIG. 12B). This cisplatin-induced cell death was blocked by exposing neuronal cultures to E3330 (20 µM) or to APX2009 (20 µM) for 48 hours prior to and throughout the cisplatin treatment (FIG. 12B). In contrast, pretreatment with 20 µM of APX2007 or APX2032 did not attenuate the cisplatin-induced cell death, with the combination of APX2032 and cisplatin (100 µM) reducing cell viability to 9±9% (FIG. 12B). Therefore, APX2009 protects sensory neuronal cultures against cisplatin-induced cell death at all dose levels used, whereas APX2007 and APX2032 caused cell killing at high dose (100 µM).

Figure 14A:
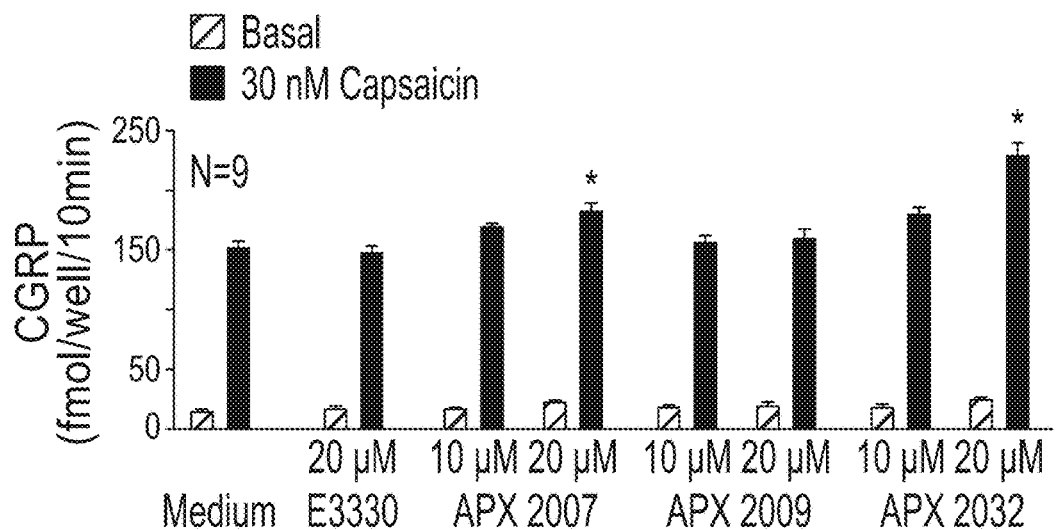
FIGS. 14A & 14B show that E3330 and APX2009 did not alter CGRP release from sensory neurons in culture, but attenuated the cisplatin-induced reduction in capsaicin-evoked release of CGRP. Each column represents the mean±SEM of basal release (open columns) or capsaicin-stimulated release (shaded columns) of CGRP in fmol/well/min.
Figure 14B:
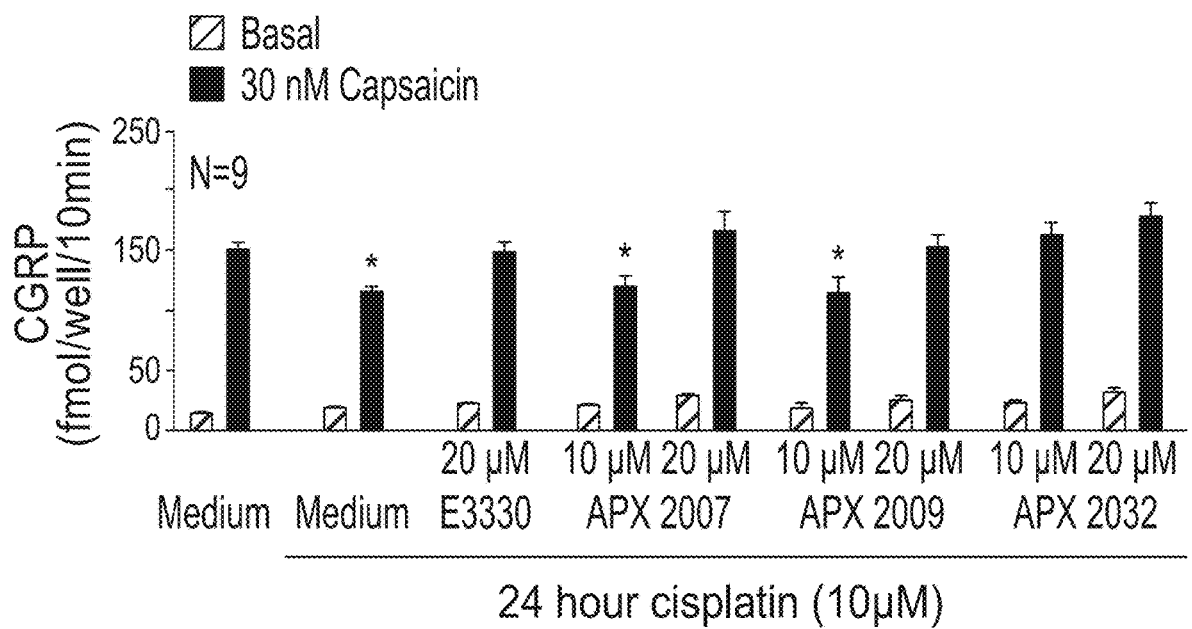

E3330 and APX2009, But Not APX2007 or APX2032, Attenuated Cisplatin-Induced Decrease in Transmitter Release from Sensory Neurons Although relatively high concentrations of cisplatin are necessary to cause cell death in sensory neuronal cultures, lower concentrations reduce transmitter release from sensory neurons. Thus, it was further determined whether E3330 analogs could attenuate a functional endpoint of cisplatin-induced neurotoxicity, i.e., the decrease in capsaicin-evoked release of CGRP. When sensory neurons in culture were exposed to E3330 (20 µM) or APX2009 (10 or 20 µM) for 72 hours and CGRP release examined, there was no significant change in either basal (resting) release or release stimulated by 30 nM capsaicin when compared untreated cells (FIG. 14A). However, pretreatment with APX2007 or APX2032 (10 µM) for 72 hours also did not affect CGRP release, whereas 20 µM of each caused a significant increase in capsaicin-stimulated release (FIG. 14A). None of the drugs at the concentrations tested altered the total content of CGRP in the cultures (data not shown). Confirming previous results, neuronal cultures exposed to 10 µM cisplatin resulted in a significant reduction in the capsaicin-evoked release of CGRP (FIG. 14B). Pretreating cultures with 20 µM of E3330 or the APX compounds for 48 hours prior to and throughout exposure to cisplatin abolished the reduction in release caused by the anticancer drug (FIG. 14B). A 72 hour treatment with 10 µM APX2007 or APX2009 did not prevent the cisplatin-induced reduction in release, but 10 µM APX2032 did block the effect of cisplatin. Since APX2007 and APX2032 alone augmented transmitter release, the reversal of the cisplatin effect could be nonspecific. In contrast, both E3330 and APX2009 appear neuroprotective since they do not alter release when given alone.

Figure 15:
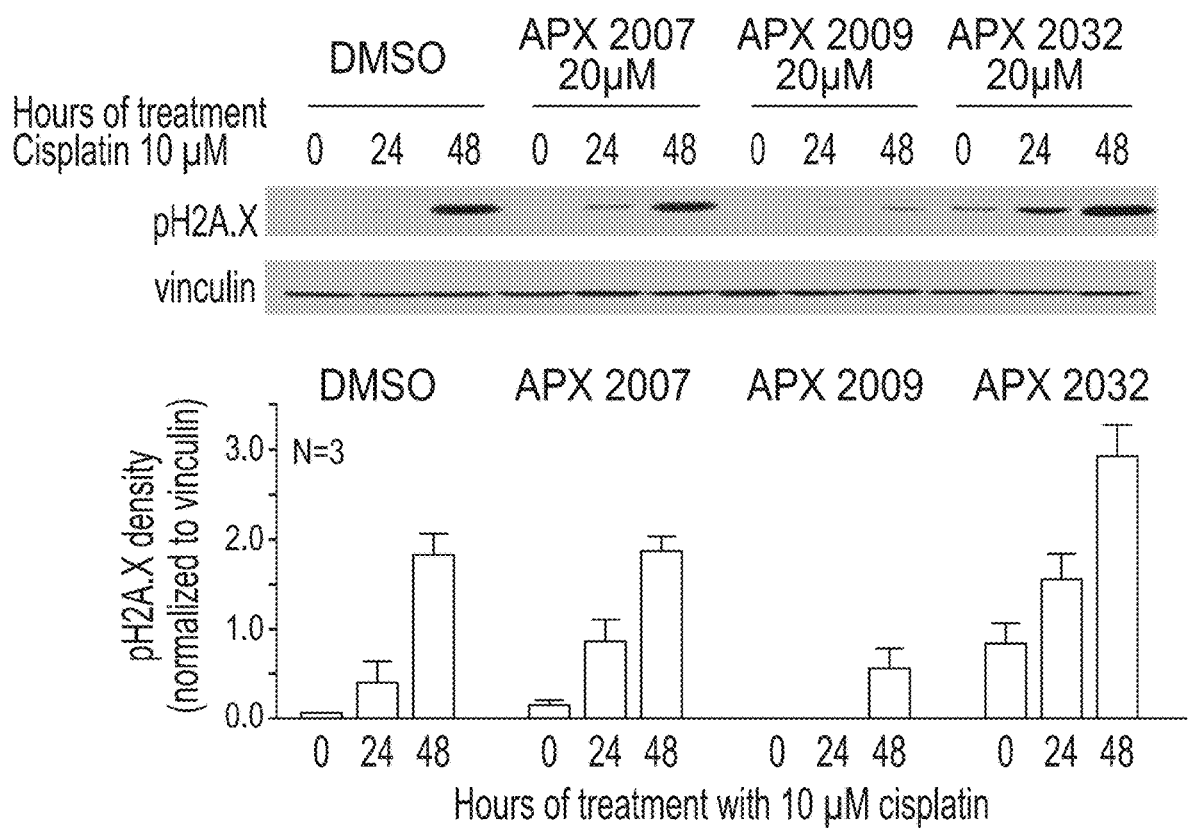
FIG. 15 shows that APX2009, but not APX2007 or APX2032, attenuated the cisplatin-induced phosphorylation of H2AX in sensory neuronal cultures. The top panel shows representative Western blots of phospho-H2AX (pH2AX) and vinculin from cultures prior to and after 24 and 48 hours of exposure to 10 µM cisplatin. Cultures were exposed to DMSO as a vehicle control or to 20 µM APX2007, APX2009 or APX2032 for 72 hours before and during cisplatin treatment as indicated. The bottom panel represents the mean±SEM of the densitometry of pH2AX expression normalized to vinculin from 3 independent experiments. An * indicates a statistically significant increase in pH2AX density in cells treated with cisplatin, whereas a † indicates a significant change by drug compared to DMSO controls at the same time points using ANOVA and Tukey's post hoc test.

APX2009 Significantly Reduced DNA Damage Induced By Cisplatin in Sensory Neuronal Cultures As further confirmation of the neuroprotective effects of APX2009 following cisplatin treatment, the levels of phospho-H2AX (pH2AX), a marker of DNA damage, were measured in sensory neuronal cultures in the absence or presence of various E3330 analogs. When cultures were exposed to 10 µM cisplatin for 24 or 48 hours, there was a significant increase in the levels of pH2AX as measured using Western blotting confirming DNA damage by the platinum compound (FIG. 15). Pretreating cultures with APX2009 (20 µM) for 48 hours prior to and throughout exposure to cisplatin significantly reduced the levels of pH2AX. In contrast, neither APX2007 nor APX2032 (20 µM) altered the ability of cisplatin to produce DNA damage (FIG. 15).

APX2009 Was Neuroprotective Against Oxaliplatin-Induced Neurotoxicity

Figure 16A:
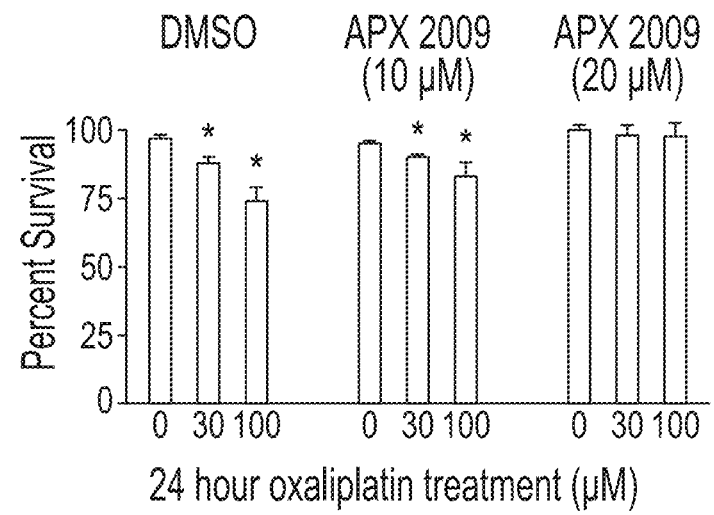
FIGS. 16A-16C show that APX2009 attenuated the oxaliplatin-induced toxicity of sensory neurons in culture.
Figure 16B:
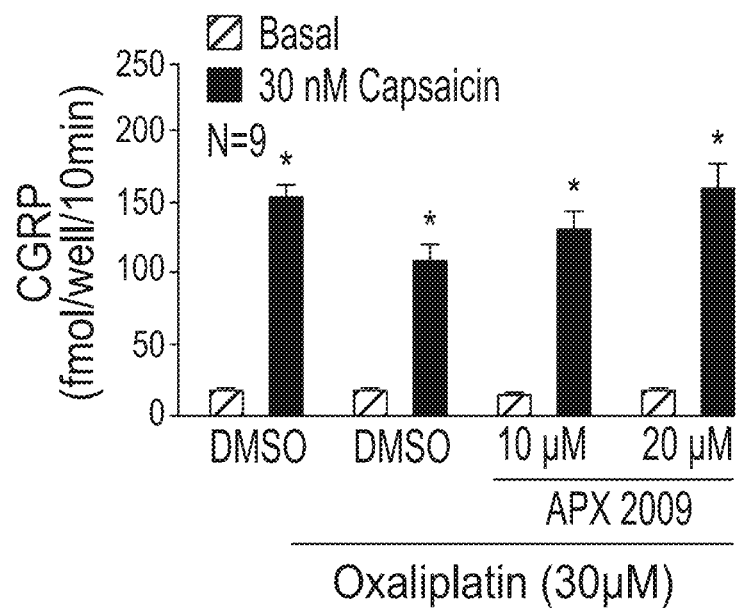

Based on the findings that APX2009, but not APX2007 and APX2032, protected against cisplatin-induced DNA damage and decreased CGRP release, APX2009 was prioritized for use in subsequent studies with another platinum agent, oxaliplatin. Cisplatin and oxaliplatin both produce significant levels of ROS in cells, with cisplatin producing higher levels. However, the DNA cross-links produced by these two agent differ: with cisplatin producing Pt-1-2-d (GpG) intrastrand DNA crosslinks while oxaliplatin creates predominantly Pt-1-3 d(ApG) interstrand DNA crosslinks. It has previously been demonstrated that E3330 protects against both cisplatin- and oxaliplatin-induced neurotoxicity. Therefore, APX2009 was analyzed to determine if it had a similar protective effect following oxaliplatin treatment, which would also support the hypothesis that it is the repair of oxidative DNA damage participates in the regulation of the platinum cross-link removal. As shown in FIG. 16A, a 72-hour treatment with 10 or 20 µM APX2009 protected the sensory neuronal cultures from cell killing caused by a 24 exposure to oxaliplatin. In a similar manner, pretreating neuronal cultures with APX2009 for 48 hours prior to and throughout exposure to oxaliplatin for 24 hours, prevented the oxaliplatin-induced decrease in CGRP release from sensory neurons (FIG. 16B).

Figure 16C:
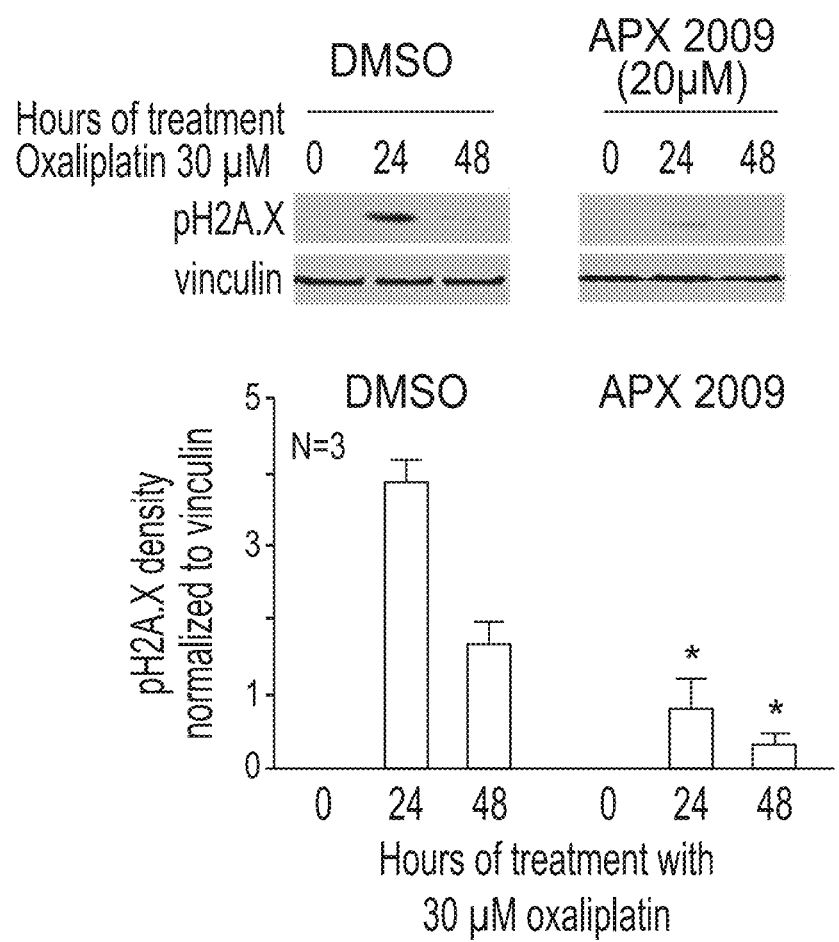

APX2009 also significantly reduced the phosphorylation of H2AX after 24 and 48 hr treatments of oxaliplatin (FIG. 16C), indicating that its neuroprotective effects may be due to reduced DNA damage.

Treatment of Human PDAC 3D Tumor Model With APX2009

Figure 17A:
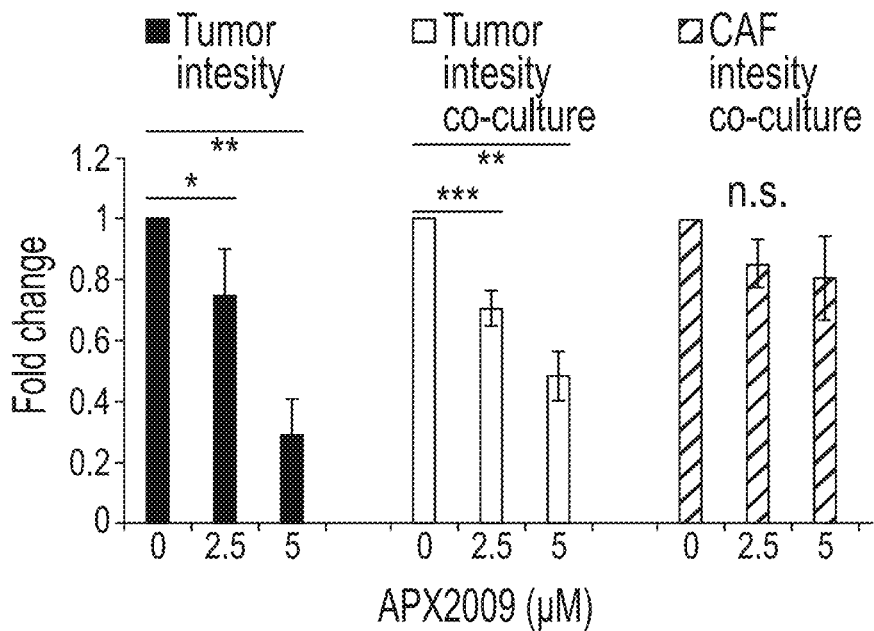
FIGS. 17A-17C depict tumor, but not CAF, cell killing by APX2009 in PDAC 3D model.
Figure 17B:
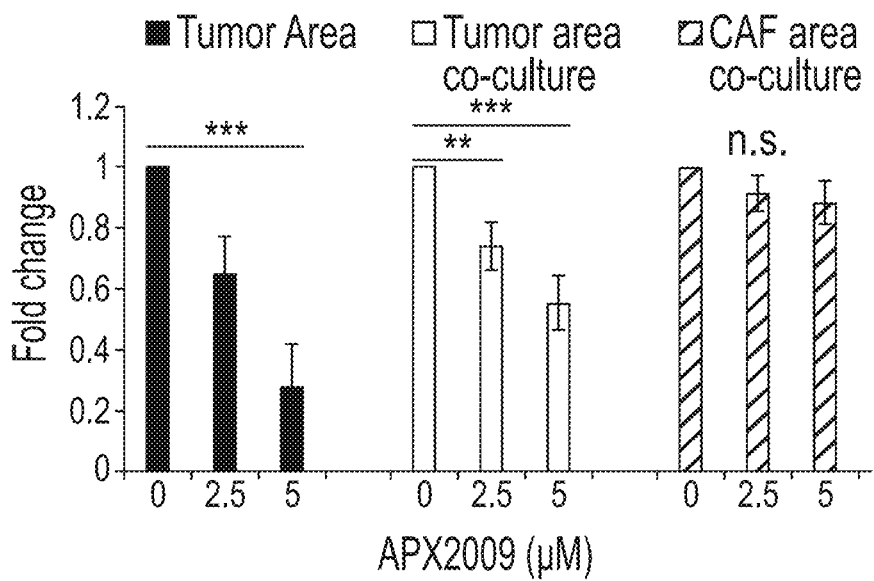
Figure 17C:
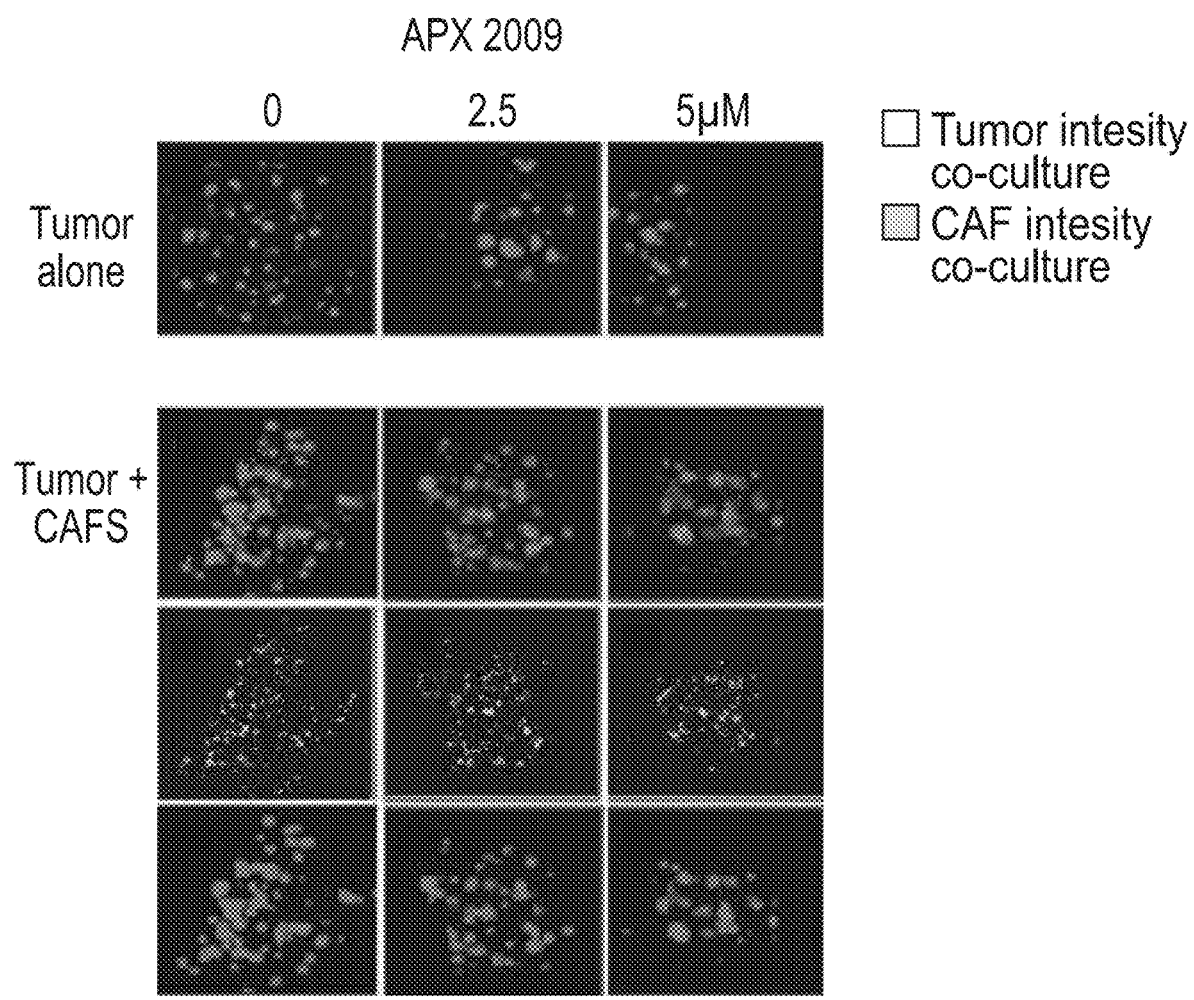

While the neuroprotective effects of APX2009 are evident, also investigated was whether these E3330 analogs were capable of tumor cell killing similar to what has been observed with E3330. A three-dimensional co-culture model of pancreatic cancer was used as an ex vivo system that included both low passage patient-derived tumor cells and cancer-associated fibroblasts. The effects of APX2009-induced cytotoxicity on the area and intensity of both tumor cells alone and in co-culture with CAFs were assessed. Spheroids composed of patient-derived PDAC cells (Pa03C-labeled red) and CAF19 cells (labeled green) were treated with APX2009, and the area and intensity of red and green fluorescence were evaluated separately as markers for each cell type (FIGS. 17A-17C). Interestingly, CAFs were not significantly affected by APX2009 treatment, again suggesting that non-tumorigenic cells can tolerate the effects of APE1 inhibition more than tumor cells. This data is similar to what is observed with E3330, but being effective at lower dose levels, validating APX2009 as a potential PDAC therapeutic agent while also showing CIPN protective indications.

What is claimed is:

1. A method of treating inflammation and chronic pain in a subject suffering from diabetes, the method comprising administering to the subject an effective amount of an apurinic/apyrimidinic endonuclease 1 redox factor 1 (APE1/Ref-1) inhibitor and at least one additional therapeutic agent selected from the group consisting of platinum drugs, taxanes, doxorubicin, alkaloids, thalidomide, lenolidomide, pomalidomide, bortexomib, carfilzomib, eribulin, ionizing radiation, cisplatin, oxaliplatin and combinations thereof, wherein the APE1/Ref-1 inhibitor is selected from the group consisting of 3-[5-(2,3-dimethoxy-6-methyl-1,4-benzoquinoyl)]-2-nonyl-2-propenoic acid], (APX3330); [(2E)-2-[(3-methoxy-1,4-dioxo-1,4-dihydronaphthalen-2-yl)methylidene]-N,N-diethylpentanamide] (APX2009), (2E)-2-[(3-methoxy-1,4-dioxo-1,4-dihydronapthalen-2-yl)methylidene]-N,N-dimethylpentanamide] (APX2007), (2E)-2-[(3-methoxy-1,4-dioxo-1,4-dihydronapthalen-2-yl)methylidene]-N-methoxypentanamide] (APX2014), (2E)-2-(3-methoxy-1,4-dioxo-1,4-dihydronaphthalen-2-yl)-N,N,2-trimethylprop-2-enamide (APX2032), pharmaceutically acceptable salts and pharmaceutically acceptable solvates thereof, and combinations thereof, pharmaceutically acceptable salts or pharmaceutically acceptable solvates thereof, which selectively inhibits the amino terminal portion of APE1.

2. The method as set forth in claim 1, wherein the APE1/Ref-1 inhibitor is selected from the group consisting of 3-[5-(2,3-dimethoxy-6-methyl-1,4-benzoquinoyl)]-2-nonyl-2-propenoic acid], (APX3330); [(2E)-2-[(3-methoxy-1,4-dioxo-1,4-dihydronaphthalen-2-yl)methylidene]-N,N-diethylpentanamide] (APX2009) and (2E)-2-[(3-methoxy-1,4-dioxo-1,4-dihydronapthalen-2-yl)methylidene]-N-methoxypentanamide] (APX2014).

3. The method as set forth in claim 1, wherein the at least one additional therapeutic agent is selected from the group consisting of platinum drugs, ionizing radiation and combinations thereof.

4. The method as set forth in claim 1, wherein the APE1/Ref-1 inhibitor is APX3330 and the subject is administered from about 5 µM to about 50 µM APX3330.

5. A method of enhancing the DNA base excision repair (BER) pathway in a subject suffering from diabetes, the method comprising administering to the subject an effective amount of an apurinic/apyrimidinic endonuclease 1 redox factor 1 (APE1/Ref-1) inhibitor and at least one additional therapeutic agent selected from the group consisting of platinum drugs, taxanes, doxorubicin, alkaloids, thalidomide, lenolidomide, pomalidomide, bortexomib, carfilzomib, eribulin, ionizing radiation, cisplatin, oxaliplatin and combinations thereof, wherein the APE1/Ref-1 is selected from the group consisting of 3-[5-(2,3-dimethoxy-6-methyl-1,4-benzoquinoyl)]-2-nonyl-2-propenoic acid], (APX3330); [(2E)-2-[(3-methoxy-1,4-dioxo-1,4-dihydronaphthalen-2-yl)methylidene]-N,N-diethylpentanamide] (APX2009), (2E)-2-[(3-methoxy-1,4-dioxo-1,4-dihydronapthalen-2-yl)methylidene]-N,N-dimethylpentanamide] (APX2007), (2E)-2-[(3-methoxy-1,4-dioxo-1,4-dihydronapthalen-2-yl)methylidene]-N-methoxypentanamide] (APX2014), (2E)-2-(3-methoxy-1,4-dioxo-1,4-dihydronaphthalen-2-yl)-N,N,2-trimethylprop-2-enamide (APX2032), pharmaceutically acceptable salts and pharmaceutically acceptable solvates thereof, and combinations thereof, pharmaceutically acceptable salts or pharmaceutically acceptable solvates thereof, which selectively inhibits the amino terminal portion of APE1.

6. The method as set forth in claim 5, wherein the APE1/Ref-1 inhibitor is selected from the group consisting of 3-[5-(2,3-dimethoxy-6-methyl-1,4-benzoquinoyl)]-2-nonyl-2-propenoic acid], (APX3330); [(2E)-2-[(3-methoxy-1,4-dioxo-1,4-dihydronaphthalen-2-yl)methylidene]-N,N-diethylpentanamide] (APX2009) and (2E)-2-[(3-methoxy-1,4-dioxo-1,4-dihydronapthalen-2-yl)methylidene]-N-methoxypentanamide] (APX2014).

7. The method as set forth in claim 5, wherein the at least one additional therapeutic agent is selected from the group consisting of platinum drugs, ionizing radiation and combinations thereof.

8. The method as set forth in claim 5, wherein the APE1/Ref-1 inhibitor is APX3330 and the subject is administered from about 5 µM to about 50 µM APX3330.

9. A method of treating inflammation and chronic pain in a subject suffering from diabetes, the method comprising administering to the subject an effective amount of an apurinic/apyrimidinic endonuclease 1 redox factor 1 (APE1/Ref-1) inhibitor selected from the group consisting of [(2E)-2-[(3-methoxy-1,4-dioxo-1,4-dihydronaphthalen-2-yl)methylidene]-N,N-diethylpentanamide] (APX2009), (2E)-2-[(3-methoxy-1,4-dioxo-1,4-dihydronapthalen-2-yl)methylidene]-N,N-dimethylpentanamide] (APX2007), (2E)-2-[(3-methoxy-1,4-dioxo-1,4-dihydronapthalen-2-yl)methylidene]-N-methoxypentanamide] (APX2014), (2E)-2-(3-methoxy-1,4-dioxo-1,4-dihydronaphthalen-2-yl)-N,N,2-trimethylprop-2-enamide (APX2032), pharmaceutically acceptable salts and pharmaceutically acceptable solvates thereof, and combinations thereof, pharmaceutically acceptable salts or pharmaceutically acceptable solvates thereof, which selectively inhibits the amino terminal portion of APE1.

10. The method as set forth in claim 9 further comprising administering at least one additional therapeutic agent selected from the group consisting of platinum drugs, taxanes, doxorubicin, alkaloids, thalidomide, lenolidomide, pomalidomide, bortexomib, carfilzomib, eribulin, ionizing radiation and combinations thereof.

11. The method as set forth in claim 9 further comprising administering at least one additional therapeutic agent selected from the group consisting of cisplatin and oxaliplatin to the subject.

12. A method of enhancing the DNA base excision repair (BER) pathway in a subject suffering from diabetes, the method comprising administering to the subject an effective amount of an apurinic/apyrimidinic endonuclease 1 redox factor 1 (APE1/Ref-1) inhibitor selected from the group consisting of [(2E)-2-[(3-methoxy-1,4-dioxo-1,4-dihydronaphthalen-2-yl)methylidene]-N,N-diethylpentanamide] (APX2009), (2E)-2-[(3-methoxy-1,4-dioxo-1,4-dihydronapthalen-2-yl)methylidene]-N,N-dimethylpentanamide] (APX2007), (2E)-2-[(3-methoxy-1,4-dioxo-1,4-dihydronapthalen-2-yl)methylidene]-N-methoxypentanamide] (APX2014), (2E)-2-(3-methoxy-1,4-dioxo-1,4-dihydronaphthalen-2-yl)-N,N,2-trimethylprop-2-enamide (APX2032), pharmaceutically acceptable salts and pharmaceutically acceptable solvates thereof, and combinations thereof, pharmaceutically acceptable salts or pharmaceutically acceptable solvates thereof, which selectively inhibits the amino terminal portion of APE1.

13. The method as set forth in claim 12 further comprising administering at least one additional therapeutic agent selected from the group consisting of platinum drugs, taxanes, doxorubicin, alkaloids, thalidomide, lenolidomide, pomalidomide, bortexomib, carfilzomib, eribulin, ionizing radiation and combinations thereof.

14. The method as set forth in claim 12 further comprising administering at least one additional therapeutic agent selected from the group consisting of cisplatin and oxaliplatin to the subject.

\* \* \* \* \*

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Synthetic

<400> SEQUENCE: 1
gucugguaag acuggaguac c          21

<210> SEQ ID NO 2
<211> LENGTH: 21
<212> TYPE: RNA
<213> ORGANISM: Artificial Sequence
<220> FEATURE:
<223> OTHER INFORMATION: Synthetic

<400> SEQUENCE: 2
ccaugagguc agcauggucu g          21

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
gcccccgggg acgtacgata tcccgctcc          29

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4
ggagcgggat atcgtacgtc ccccgggggc          30